(12) United States Patent
Ishidoya et al.

(10) Patent No.: US 6,627,902 B2
(45) Date of Patent: Sep. 30, 2003

(54) DOSE READING DEVICE AND DOSE READING MAGAZINE

(75) Inventors: Tatsuyo Ishidoya, Fujieda (JP); Motoyuki Sato, Shizuoka (JP)

(73) Assignee: Asahi Techno Glass Corporation, Chiba (JP)

( * ) Notice: Subject to any disclaimer, the term of this patent is extended or adjusted under 35 U.S.C. 154(b) by 0 days.

(21) Appl. No.: 10/022,000

(22) Filed: Dec. 14, 2001

(65) Prior Publication Data

US 2003/0047690 A1 Mar. 13, 2003

(30) Foreign Application Priority Data

| Sep. 4, 2001 | (JP) | ........................................ 2001-267108 |
| Sep. 4, 2001 | (JP) | ........................................ 2001-267117 |
| Sep. 4, 2001 | (JP) | ........................................ 2001-267127 |
| Sep. 5, 2001 | (JP) | ........................................ 2001-268295 |

(51) Int. Cl.$^7$ ................................................. G01T 1/06
(52) U.S. Cl. ...................................... 250/484.5; 250/328
(58) Field of Search ............................ 250/328, 461.1, 250/472.1, 473.1, 484.2, 484.5; 264/21, 405, 239, 319, 320, 339

(56) References Cited

U.S. PATENT DOCUMENTS

| 4,318,615 A | * | 3/1982 | Sagusa et al. ............... 250/328 |
| 4,377,751 A | * | 3/1983 | Kronenberg et al. ...... 250/472.1 |
| 4,722,607 A | * | 2/1988 | Anselment et al. ....... 250/461.1 |
| 4,725,388 A | * | 2/1988 | Nelson et al. ................. 264/21 |
| 5,057,693 A |   | 10/1991 | Burgkhardt et al. |
| 5,225,680 A | * | 7/1993 | Yrjonen et al. ............. 250/328 |
| 5,281,394 A | * | 1/1994 | Holub ........................ 250/328 |
| 6,268,602 B1 | * | 7/2001 | Seiwatz et al. .......... 250/473.1 |

FOREIGN PATENT DOCUMENTS

| JP | 5142352 | 6/1993 |
| JP | 6138235 | 5/1994 |

* cited by examiner

Primary Examiner—G. Bradley Bennett

(57) ABSTRACT

A dose reading device comprises: an ultraviolet irradiating section 40 for irradiating an ultraviolet laser beam forming an excitation light source for fluorescent glass elements X; a fluorescence detecting section 50 for detecting a radiation exposure dose from the intensity of fluorescence generated by a fluorescent glass element X; a magazine conveying section 30 for conveying a magazine 10 capable of accommodating a plurality of fluorescent glass elements X to a position for measurement by the fluorescence detecting section 50; a dark box for accommodating the magazine conveying section 30 and the fluorescence detecting section 50; a first shielding plate 31c set at a non-perpendicular angle to the light axis of the ultraviolet laser beam having passed through the fluorescent glass element X; a second shielding plate 31e for shielding fluorescence from the fluorescent glass elements X other than the fluorescent glass element X under measurement; and first and second slit plates 41a, 42a for transmitting only ultraviolet light that is directed at the fluorescent glass element X under measurement.

21 Claims, 22 Drawing Sheets (A)

(B)

(A)

(B)

Y (DISH SHAPE)

Z (DOMED SHAPE)

(DISH SHAPE) Y

10

Z
(DOMED SHAPE)

(A)    (B)

DOSE READING DEVICE AND DOSE READING MAGAZINE

BACKGROUND OF THE INVENTION

The present invention relates to a dose reading device for a fluorescent glass dosimeter detecting the intensity of fluorescence generated upon excitation by ultraviolet light, and more particularly, to a dose reading device having an improved fluorescence reading system for a multiplicity of fluorescent glass elements accommodated in a magazine. Furthermore, the present invention relates to a magazine capable of accommodating a multiplicity of fluorescent glass elements which generate fluorescence upon excitation by ultraviolet light, and more particularly, to a dose reading magazine and a method of manufacture for same, whereby the fluorescence can be read off while the aforementioned elements are accommodated in the magazine. Moreover, the present invention relates to a dose reading magazine, dose reading method and dose reading device, whereby reading of high doses can be performed. Furthermore, the present invention also relates to a dose reading device whereby the weak fluorescence from compact fluorescent glass elements is gathered efficiently, and hence detection sensitivity is improved.

In the installation and operation of facilities such as nuclear reactors, accelerators, X-ray generators, and radio isotopes, it is necessary to achieve complete safety in radiation management, in order to protect human beings from radioactivity. In particular, management must be provided to ensure that the radiation dose to which the employees working in various fields in the aforementioned facilities, and the users of the facilities, are exposed comes within a prescribed tolerance range. Dosimeters are used for radiation management of this kind. These dosimeters are located in prescribed locations within a facility, and/or are carried by employees and users, and by reading out the respective exposure doses thereof at regular intervals, it is possible to manage the radiation doses to which employees and users are exposed.

One type of generally used dosimeter is a fluorescent glass dosimeter. In general, a fluorescent glass dosimeter uses glass elements made from phosphate glass containing silver ions. After being irradiated with radiation and activated, these glass elements generate a phenomenon (radio photo luminescence:RPL) whereby they produce fluorescence when excited by ultraviolet radiation of wavelength 300–400 nm. Since the intensity of the fluorescence produced is directly proportional to the radiation exposure dose received by the relevant glass element, it is possible to measure the radiation exposure dose by detecting the intensity of the fluorescence. A particular feature of fluorescent glass dosimeters of this kind is that they can be read out repeatedly, without the core which generates RPL being destroyed by the reading operation.

In measurement using a fluorescent glass dosimeter of this kind, the light emitted by the ultraviolet excitation light source is passed through an optical filter to selectively extract ultraviolet light of prescribed wavelengths, and is then incident on one face of the fluorescent glass elements. The fluorescent light consequently generated by the fluorescent glass dosimeter is passed through an optical filter to selectively transmit light in a prescribed wavelength range, whereupon it is opto-electrically converted by an photomultiplier tube to obtain an electrical signal having a level that is roughly proportional to the fluorescence intensity, and the fluorescence intensity, and hence the radiation exposure dose is measured from the level of the electrical signal.

In general, as illustrated in FIG. 27, a dose reading device for reading out the radiation exposure dose according to the principles described above uses a magazine 3 accommodating a multiplicity of capsules 1 holding a fluorescent glass element 2 therein. This magazine 3 is loaded onto a magazine conveying device 4 by a magazine supply device (not illustrated), and conveyed to a prescribed position. The fluorescent glass elements 2 are then extracted, one by one, from their respective capsules 1, by means of an extracting device (not illustrated), conveyed to a fluorescence detection position which is shielded from external light, and then are subjected to ultraviolet irradiation and fluorescence quantity detection.

However, a conventional dose reading device as described above involves the following kinds of problems. Specifically, since the fluorescent glass elements accommodated in the magazine must be taken out from the magazine, one by one, and transported to a reading position, in order to perform fluorescence reading, a large amount of time is required to read out the fluorescence quantity of a multiplicity of fluorescent glass elements.

Furthermore, during extraction of the individual fluorescent glass elements from the magazine, or during conveyance thereof, transportation problems may occur, such as the elements catching on surrounding members, or the like. In particular, since the small-sized fluorescent glass elements, described hereinafter, are simple glass elements and do not have a metal frame, or the like, then if a transportation problem arises during loading thereof into a conventional reading device, there is a very high risk of problems such as breaking of the glass, soiling of the surfaces thereof, or degradation of the fluorescence-based measurement accuracy due to the presence of foreign matter.

Furthermore, since a mechanism is required for extracting the fluorescent glass elements individually, there are drawbacks in that the manufacturing costs rise and the size of the overall device increases. In particular, in a dose reading system using small-sized fluorescent glass dosimeters, as used in diagnostic and medical dose evaluation, animal experiment dose evaluation, and various other types of experiments, and the like, since the fluorescent glass elements are very small, they are extremely difficult to extract mechanically.

Moreover, as described above, a dose reading device generally uses a magazine 3 accommodating a multiplicity of fluorescent glass elements 2 held in capsules 1, as illustrated in FIG. 27 and FIG. 28. This magazine 3 is loaded from a magazine supply device (not illustrated) onto a magazine conveying device 4 and conveyed to a prescribed position, where the fluorescent glass elements 2 are extracted from their respective capsules 1, one at a time, by an extracting device (not illustrated), and then conveyed to a fluorescence detection position which is shielded from external light, where they are subjected to ultraviolet irradiation and fluorescence quantity detection. From the viewpoint of moldability, PS (polystyrene), for example, is used as the material for this magazine 3.

However, since the fluorescent glass elements accommodated in a conventional dose reading magazine of the kind described above must be taken out from the magazine, one by one, and transported to a fluorescent reading position, in order to perform fluorescence reading, a large amount of time is required to read out the fluorescence quantity of a multiplicity of fluorescent glass elements.

Furthermore, during extraction of the individual fluorescent glass elements from the magazine, or during conveyance thereof, transportation problems may occur, such as the elements catching on surrounding members, or the like. In particular, since the small-sized fluorescent glass elements, described hereinafter, are simple glass elements and do not have a metal frame, or the like, then if a transportation problem arises during loading thereof into a conventional reading device, there is a very high risk of problems such as breaking of the glass, soiling of the surfaces thereof, or degradation of the fluorescence-based measurement accuracy due to the presence of foreign matter.

Furthermore, since a mechanism is required for extracting the fluorescent glass elements individually, there are drawbacks in that the manufacturing costs rise and the size of the overall device increases. In particular, in a dose reading system using small-sized fluorescent glass dosimeters, as used in diagnostic and medical dose evaluation, animal experiment dose evaluation, and various other types of experiments, and the like, since the fluorescent glass elements are extremely small, they are extremely difficult to extract mechanically.

In recent years, small-sized fluorescent glass dosimeters have been used in dose evaluation for radiation therapy and diagnosis, dose measurement in animal experiments, precise dose distribution measurement and other various types of experiments, and the like. In measurement using small-sized fluorescent glass dosimeters of this kind, at high radiation exposures of 2 Gy or above, coloration of the fluorescent core in the fluorescent glass element occurs, thereby causing an ultraviolet absorbing action, and hence the exciting ultraviolet radiation required to generate fluorescence becomes attenuated inside the fluorescent glass elements. Consequently, fluorescence readings of 2 Gy or above are corrected by means of a linear correction equation.

However, in a dose reading method for conventional fluorescent glass dosimeters, as described above, if the exposure reaches 10 Gy or above, then there is marked attenuation of the exciting ultraviolet radiation and moreover, if the exposure reaches 100 Gy or above, then the amount of fluorescence conversely begins to decline. Therefore, it becomes impossible to perform correction by means of a linear correction equation, and hence it becomes difficult to measure radiation exposure doses accurately.

Furthermore, the fluorescent glass elements used in a small-sized fluorescent glass dosimeter as described above are extremely small in size. Therefore, the volume thereof which can be excited by the ultraviolet radiation is small, the incident light to the photomultiplier tube is small, and hence adequate sensitivity cannot be obtained when using a fluorescence reading device similar to the prior art.

In this case, since the light receiving surface of the photomultiplier tube, which forms the fluorescence detecting element, is greater than the fluorescent glass element, it is conceivable to adopt means for ensuring the quantity of incident light by shortening the distance between the fluorescent glass element and the photomultiplier tube. However, by shortening the distance between the fluorescent glass element X and the photomultiplier tube 51, the angle of the fluorescent light incident on the photomultiplier tube 51 is increased, as illustrated in FIG. 29. Therefore, when an interference filter 54 is inserted between the fluorescent glass element X and the photomultiplier tube 51, the amount of fluorescent light incident obliquely on the interference filter 54 is increased, and hence the transmission wavelength of the interference filter 54 is shifted to a shorter wavelength and the original selected transmission characteristics cannot be obtained.

The present invention has been devised in order to solve the aforementioned problems of the prior art, a first object thereof being to provide a dose reading device capable of making accurate dose readings while fluorescent glass elements are accommodated in a magazine.

A second object of the present invention is to provide a dose reading magazine and method of manufacturing same, whereby dose reading can be performed while fluorescent glass elements are accommodated in the magazine.

A third object of the present invention is to provide a high dose reading magazine, high dose reading method, and high dose reading device, whereby linear correction can be performed even in the case of high exposure doses, and hence radiation exposure doses can be read accurately.

A fourth object of the present invention is to provide a dose reading device whereby high detection sensitivity can be achieved by condensing weak light from a small-sized fluorescent glass element.

SUMMARY OF THE INVENTION

In order to achieve the first object, the present invention provides a dose reading device having an irradiating means for irradiating ultraviolet light forming an excitation light source for a fluorescent glass element, and a detecting means for detecting a radiation exposure dose from the intensity of fluorescence generated by said fluorescent glass element, comprising: a magazine conveying section for conveying a magazine capable of accommodating a plurality of fluorescent glass elements to the position of a fluorescence detecting part for fluorescence detection by said detecting means; and a dark box section for accommodating said magazine conveying section and said fluorescence detecting part.

According to this dose reading device, since the magazine conveying section is located inside the dark box section along with the fluorescence detecting part, it becomes possible to perform ultraviolet irradiation and fluorescence quantity reading while the fluorescent glass elements are accommodated inside the magazine, and hence there is no requirement for devices or labor to extract the fluorescent glass elements from the magazine.

In order to achieve the second object, the present invention provides a dose reading magazine having loading sections capable of loading a plurality of fluorescent glass elements for reading a radiation exposure dose from the intensity of fluorescence generated upon irradiation of ultraviolet light, comprising: an aperture window, which is provided in a prescribed position of said magazine, for allowing the fluorescence generated by said fluorescent glass elements to exit therethrough.

According to this aspect of the present invention, since the fluorescence generated by the fluorescent glass element when it is excited by irradiation of ultraviolet light while in a loaded state in the loading section is emitted via an aperture window to fluorescence detecting means, it is possible to read the radiation exposure dose without taking out the fluorescent glass elements from the magazine. Consequently, no time is taken in the reading task and conveyance problems can also be prevented.

In order to achieve the third object, the present invention provides a dose reading magazine capable of loading a fluorescent glass element which generates fluorescence corresponding to the radiation exposure dose thereof, upon irradiation of ultraviolet light, comprising: an apertures for allowing only fluorescence from an end portion of said fluorescent glass element on the side of incidence of the ultraviolet light to exit therethrough.

According to this dose reading magazine, since it is possible to read only the fluorescence from the end portion of the fluorescent glass element on the side of incidence of the ultraviolet light, where there is relatively little attenuation of the excitation ultraviolet light, then even at radiation doses of 100 Gy and above, there is no inverse decline in the amount of fluorescence. In other words, the amount of fluorescence does not reach a maximum value, but rather keeps increasing steadily, and hence correction by means of a linear correction formula can be performed, and even high doses of 100 Gy and above can be measured.

In order to achieve the fourth object, the present invention provides a dose reading device having a detecting means for detecting the radiation exposure dose of a fluorescent glass element on the basis of the intensity of the fluorescence generated by the fluorescent glass element when irradiated with ultraviolet light, comprising: a condensing means, which is provided between the fluorescent glass element under detection and said detecting means, for condensing the fluorescence generated by said fluorescent glass element.

According to this dose reading device, even if the fluorescence generated by the small-sized fluorescent glass element is very weak, since it is condensed by the condensing means, sufficient incident light to the detecting means is guaranteed, and hence high detection sensitivity can be obtained.

BRIEF DESCRIPTION OF THE DRAWINGS

FIG. 1(A) is a perspective view and FIG. 1(B) is a principal enlarged perspective view;

FIG. 9(A) is a perspective view and FIG. 9(B) is a principal enlarged perspective view;

FIG. 14(A) is a perspective view and FIG. 14(B) is a partial enlarged perspective view;

FIG. 15(A) is a perspective view and FIG. 15(B) is a partial enlarged perspective view;

FIG. 19(A) is a normal dose reading magazine; and FIG. 19(B) is a high dose reading magazine;

FIG. 26(A) is a hemispherical lens; and FIG. 26(B) is an aspherical lens;

DETAILED DESCRIPTION

Below, embodiments of a dose reading device, dose reading magazine, and the like, relating to the present invention are described concretely with reference to the drawings.

[A. Dose Reading Device]

(A-1) Composition

Figure 1:
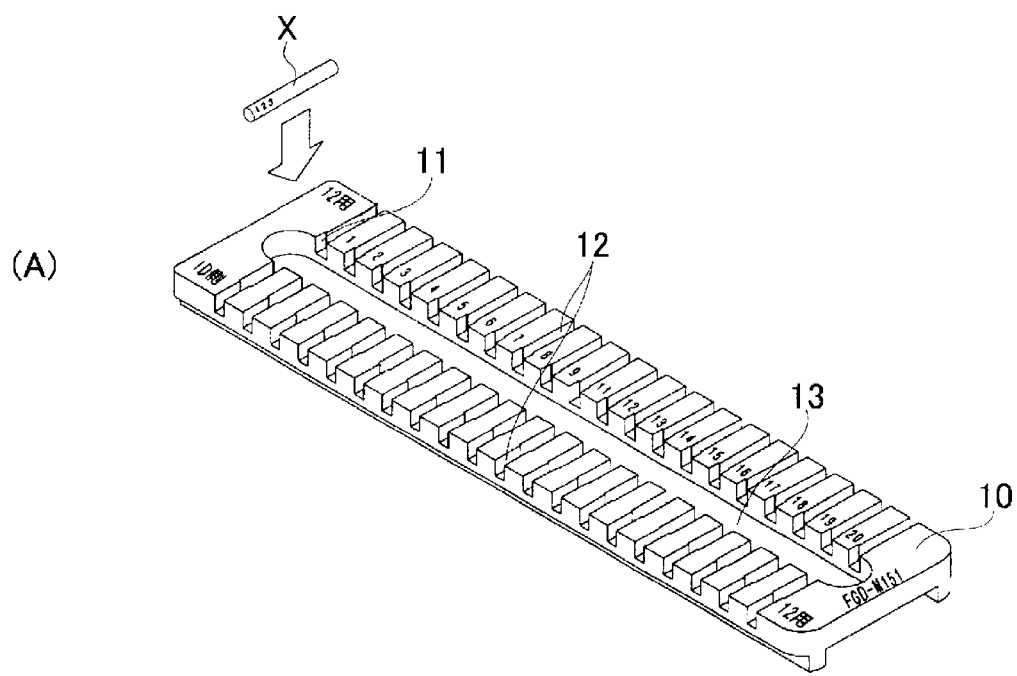
FIG. 1 is a diagram showing the composition of a magazine employed in the dose reading device according to the present invention.
Figure 1:
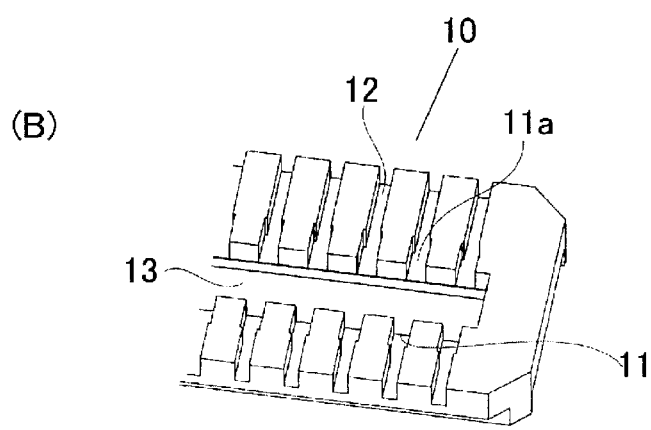
Figure 2:
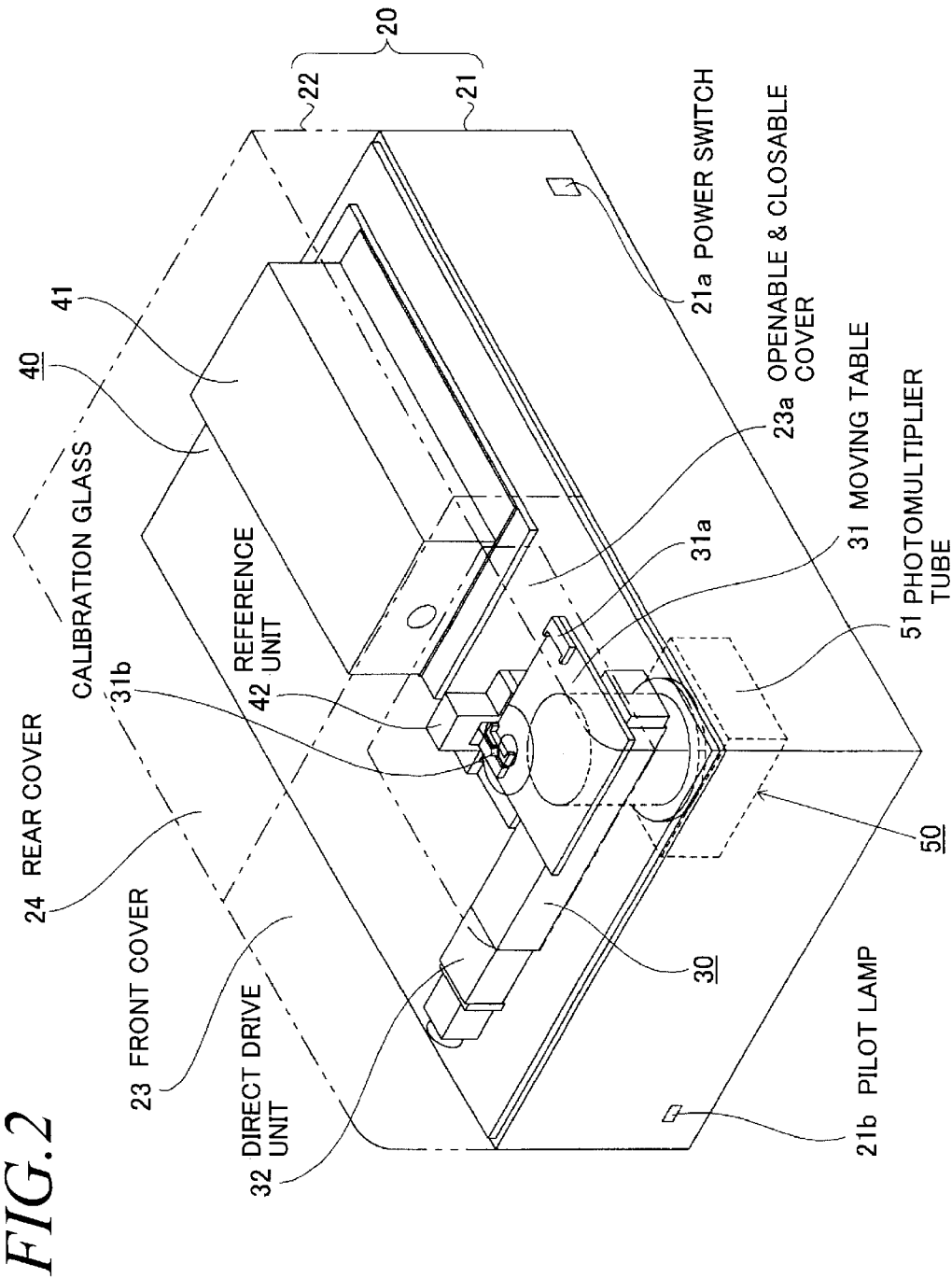
FIG. 2 is a perspective diagram showing the composition of one embodiment of a dose reading device relating to the present invention.

As shown in FIG. 1, the dose reading device according to the present embodiment uses a magazine 10 capable of accommodating a multiplicity of fluorescent glass elements X, and is composed in such a manner that the radiation exposure dose of each individual fluorescent glass element X can be read while the fluorescent glass elements X are in an accommodated state in the magazine 10. More specifically, as illustrated in FIG. 2, the dose reading device according to the present embodiment is broadly constituted by a main unit 20, a magazine conveying section 30 for conveying a magazine 10 set on a moving table to a fluorescence reading position, an ultraviolet irradiating section 40 for emitting ultraviolet light in order to irradiate the fluorescent glass elements X, and a fluorescence detecting section 50 for detecting the fluorescent light generated by the fluorescent glass elements X. The composition of each respective section is described below.

(A-1-1) Composition of Magazine

Firstly, the composition of the magazine 10 will be described. As illustrated in FIG. 1(A), this magazine 10 has a thin rectangular parallelepiped shape and is made of resin, and incorporates twenty loading sections 11 for loading the fluorescent glass elements X, disposed in parallel fashion to the shorter edges thereof. As shown in FIG. 1(B), recess-shaped grooves 11a for holding either end of a fluorescent glass element X are formed in each loading section 11. Furthermore, cutaway sections 12 forming respective light paths are formed on the line of extension of the longitudinal axis of each respective loading section 11, in order that an ultraviolet laser beam from the ultraviolet irradiating section 40 can enter and exit therethrough. Identification numbers from 1 to 20 are attached to these loading sections 11.

Moreover, an aperture window 13 which spans the plurality of fluorescent glass elements X is provided in the base side of the magazine 10, in such a manner that it transects the central portions of the fluorescent glass elements X held in the loading section 11. This aperture window 13 eliminates the effects of light reflection from the end faces, in order to function as a fluorescence detection hole, and it is formed continuously and integrally in the longitudinal direction of the magazine 10, in order that the fluorescent glass elements X can be held readily. This aperture window 13 can also be formed individually for each respective loading section 11, but in this case, desirably, the respective aperture windows 13 are formed so as to have a uniform area, in order to prevent variations in measurement accuracy.

For the fluorescent glass elements X accommodated in the magazine 10 described above, it is possible to use, for example, small-sized elements having a diameter of approximately 1.5 mm.

(A-1-2) Main Unit

Next, the main unit 20 of the dose reading device will be described. As shown in FIG. 2, the main unit 20 is constituted by a box-shaped case section 21 in which the magazine conveying section 30, ultraviolet irradiating section 40 and fluorescence detecting section 50 are provided, and a cover section 22 covering these members. The cover section 22 consists of a front cover 23 and rear cover 24, and a dark box covering the magazine conveying section 30 and the fluorescence detecting section 50 is formed inside the front cover 23. An openable and closable door cover 23a is provided on the front cover 23 in a position corresponding to the region above the fluorescence detecting section 50. In the diagram, 21a and 21b are respectively a power switch for switching on/off the power of the present device, and a pilot lamp for indicating the power on/off status thereof.

(A-1-3) Magazine Conveying Section

Figure 3:
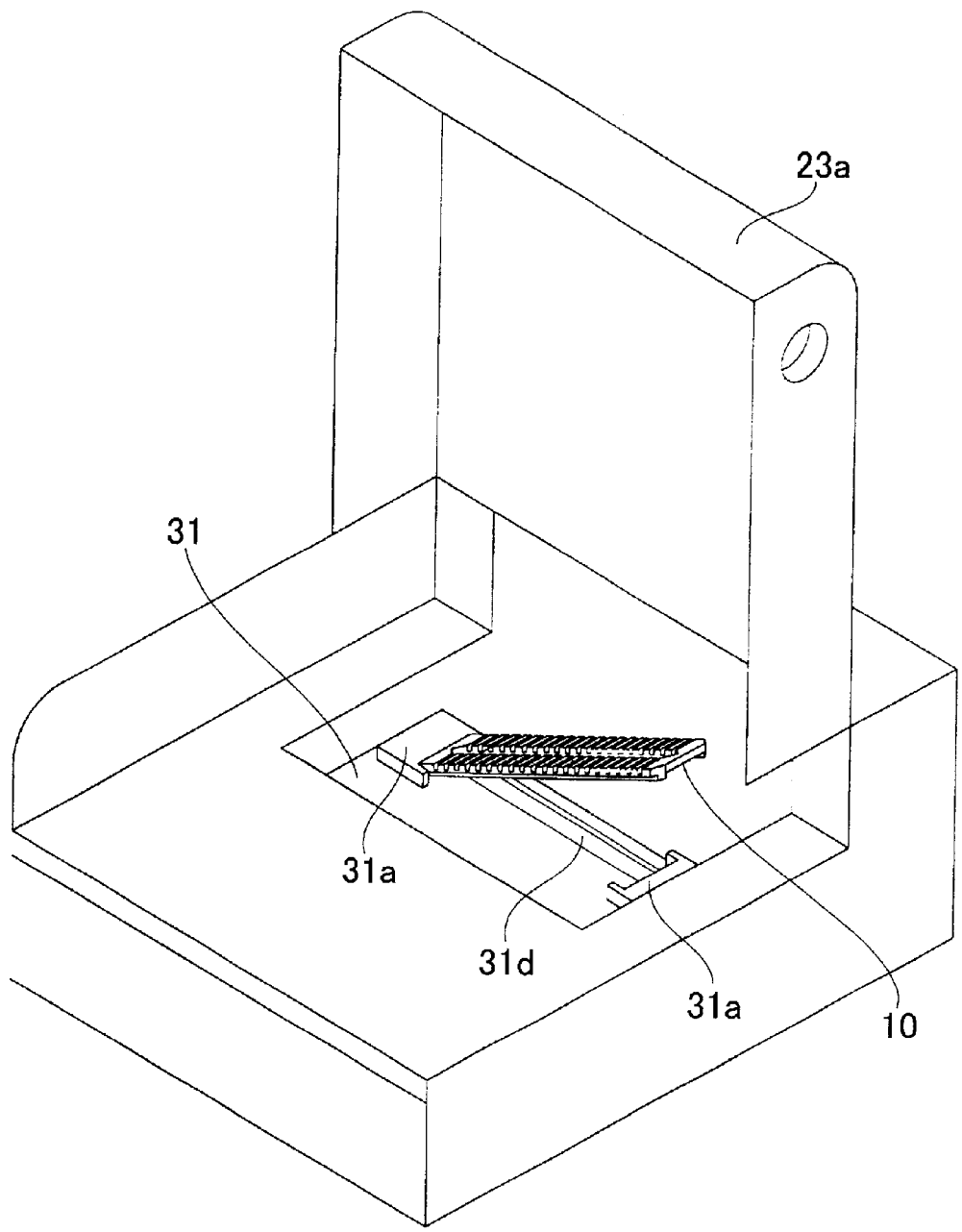
FIG. 3 is a perspective diagram illustrating a magazine accommodating method according to the embodiment in FIG. 2.

As illustrated in FIG. 2, the magazine conveying section 30 is disposed on the upper face of the case section 21, and comprises a moving table 31, whereon the magazine 10 is placed, which moves the individual fluorescent glass elements X accommodated inside the magazine 10 to a measurement position, and a direct drive unit 32 for causing the moving table 31 to move horizontally. Moreover, holders 31a for holding the magazine 10 and a calibration glass 31b, which is a standard glass for calibrating the detection sensitivity, are provided on the moving table 31. As shown in FIG. 3, the holders 31a are members which hold either end of the magazine 10 in such a manner that the longitudinal direction of the fluorescent glass elements X is perpendicular to the direction of movement of the moving table 31.

Figure 4:
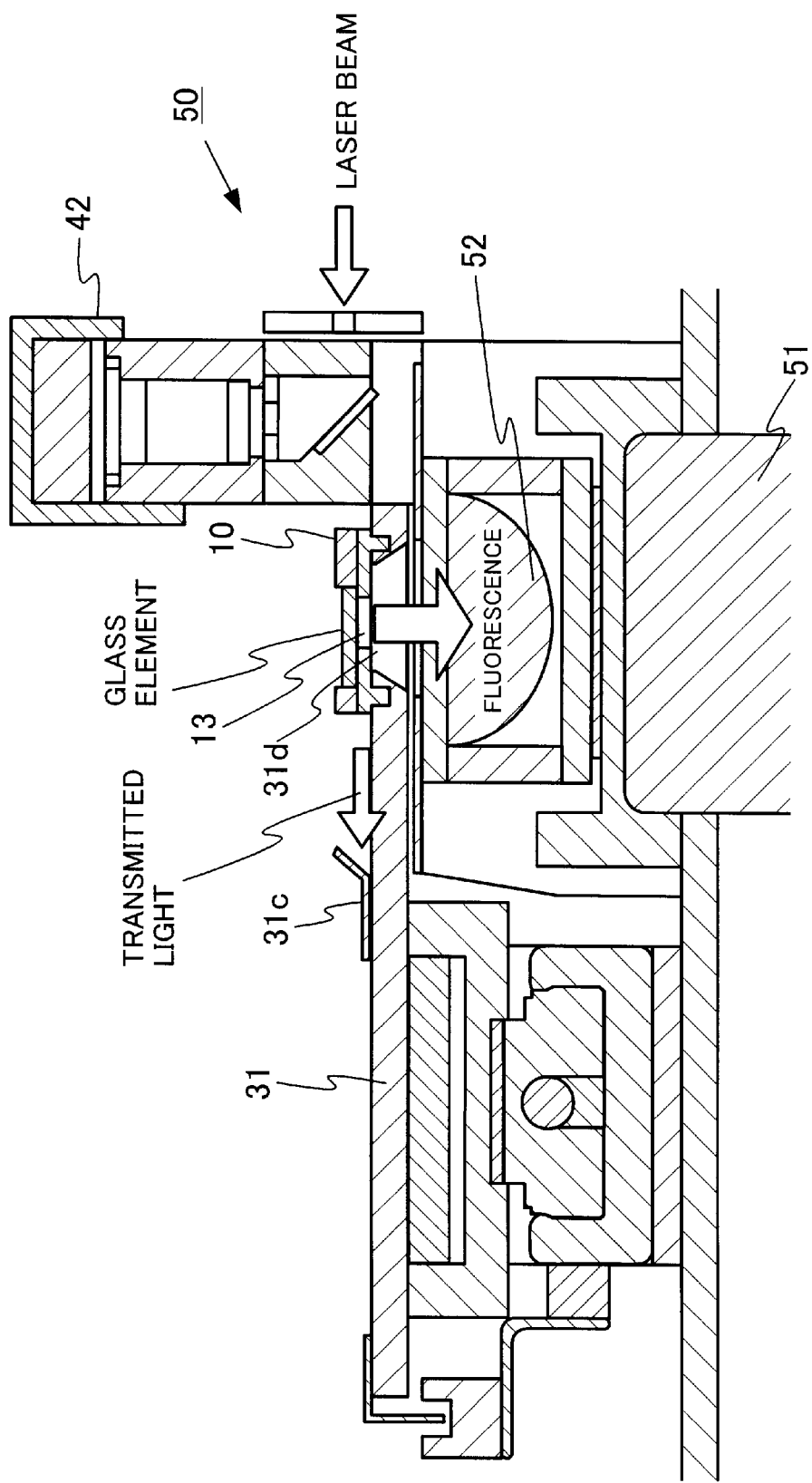
FIG. 4 is a vertical sectional diagram showing the periphery of the measurement position in the embodiment in FIG. 2.
Figure 5:
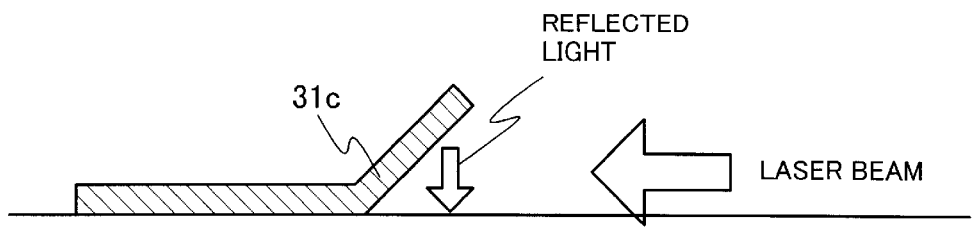
FIG. 5 is an enlarged sectional view showing the composition of the first shielding plate illustrated in FIG. 4.

Moreover, as shown in FIG. 4 and FIG. 5, a first shielding plate 31c is provided on the upper face of the moving table 31. This first shielding plate 31c is provided in a position where the ultraviolet laser beam irradiated by the ultraviolet irradiating section 40 passes through the fluorescent glass elements X. Moreover, the surface of the first shielding plate 31c which reflects the laser beam is set to a non-perpendicular angle with respect to the light axis of the laser beam, as illustrated in FIG. 5, and it is treated to reduce the surface reflectivity thereof.

Satisfactory functionality of the first shielding plate 31c can be achieved by using black Alumite obtained by generic Alumite processing of aluminium alloy. Moreover, it is also possible to use an iron material with a black electro-galvanization coating (Unichrome plating).

Figure 6:
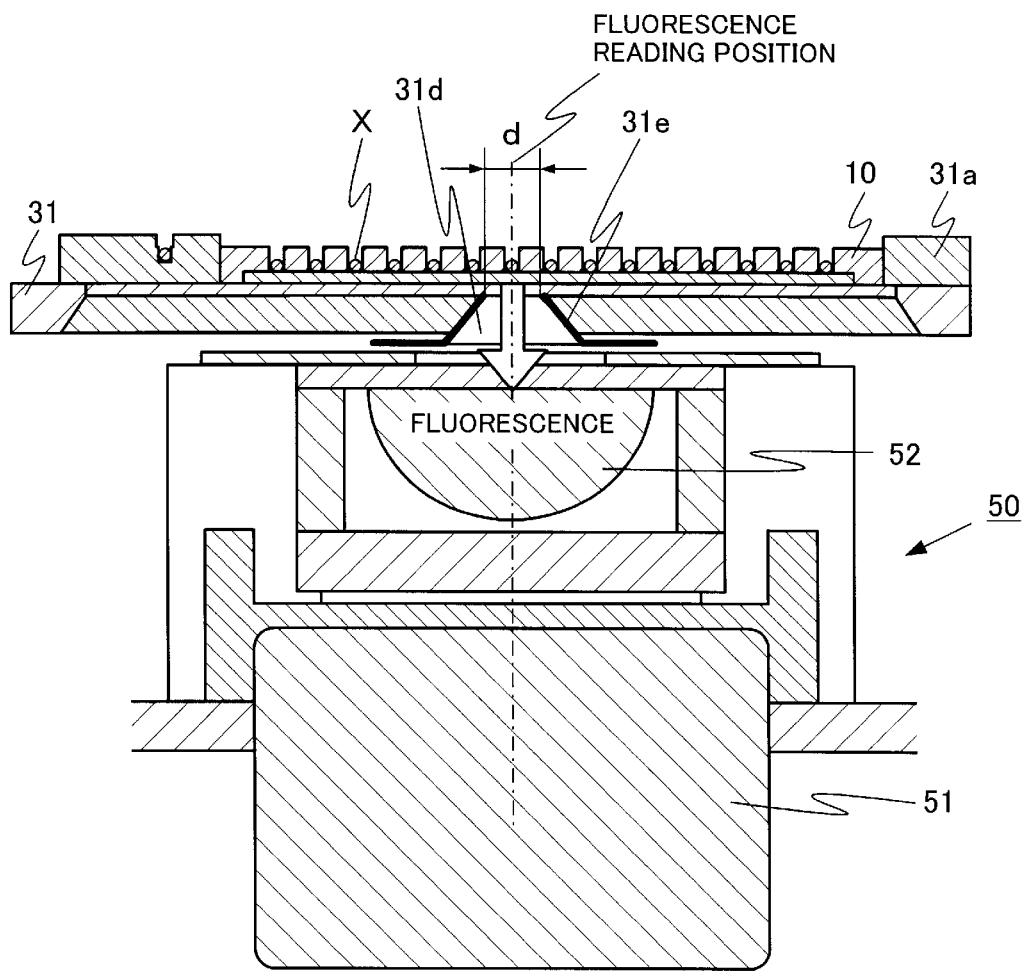
FIG. 6 is a vertical sectional view showing the periphery of a fluorescence detecting section in the embodiment in FIG. 2.

Moreover, as shown in FIG. 4 and FIG. 6, a fluorescence transmission window 31d for transmitting fluorescence generated by the fluorescent glass elements X is formed in the moving table 31, in a position corresponding to the aperture window 13 of the magazine 10 held in the holders 31a. Normally, the light receiving surface of the photomultiplier tube forming the fluorescence detecting element is greater than that of the fluorescent glass elements X, and hence the aforementioned fluorescence transmission window 31d is formed with a taper broadening at the side thereof adjacent to the fluorescence detecting section 50, in such a manner that the fluorescence from the fluorescent glass elements X is incident on the fluorescence detecting element to the full. Furthermore, as shown in FIG. 6, a second shielding plate 31e is provided in the fluorescence transmission window 31d, running in the axial direction of the fluorescent glass elements X. By means of this second shielding plate 31e, a composition is achieved whereby only the fluorescence from one of the fluorescent glass elements X is transmitted to the fluorescence detecting section 50, while the fluorescence from other adjacently positioned fluorescent glass elements X can be shielded.

The aperture dimension (d in FIG. 6) of this second shielding plate 31e varies according to the size of the fluorescent glass elements X and the pitch at which they are disposed, but it can be taken as being 4.5–5.0 mm, for example. Furthermore, in order to shield the fluorescence from fluorescent glass elements X other than that being measured, the upper end of the second shielding plate 31e is desirably positioned as closely as possible to the fluorescent glass elements X. For this second shielding plate 31e, it is possible to use a cold rolled steel plate (SPCC), which is weldable to other members, that has been treated with a black electro-galvanization coating (Unichrome plating), but an aluminium alloy, black Alumite, or the like, may also be used.

Furthermore, the drive method of the moving table 31 based on the direct drive unit 32 illustrated in FIG. 2 is a ball screw-based linear drive method using a motor as a drive source, positional control being performed by motor pulse control from a microcomputer. A composition is adopted whereby the fluorescent glass elements X in the magazine 10 held by the holders 31a, and the calibration glass 31b, are registered in positions where they can be respectively irradiated with ultraviolet light, and the fluorescence thereof can be detected, according to the movement of the moving table 31 by means of the direct drive unit 32. Positional accuracy in the movement direction can be taken as ±0.01 mm, for example.

(A-1-4) Ultraviolet Irradiating Section

Figure 7:
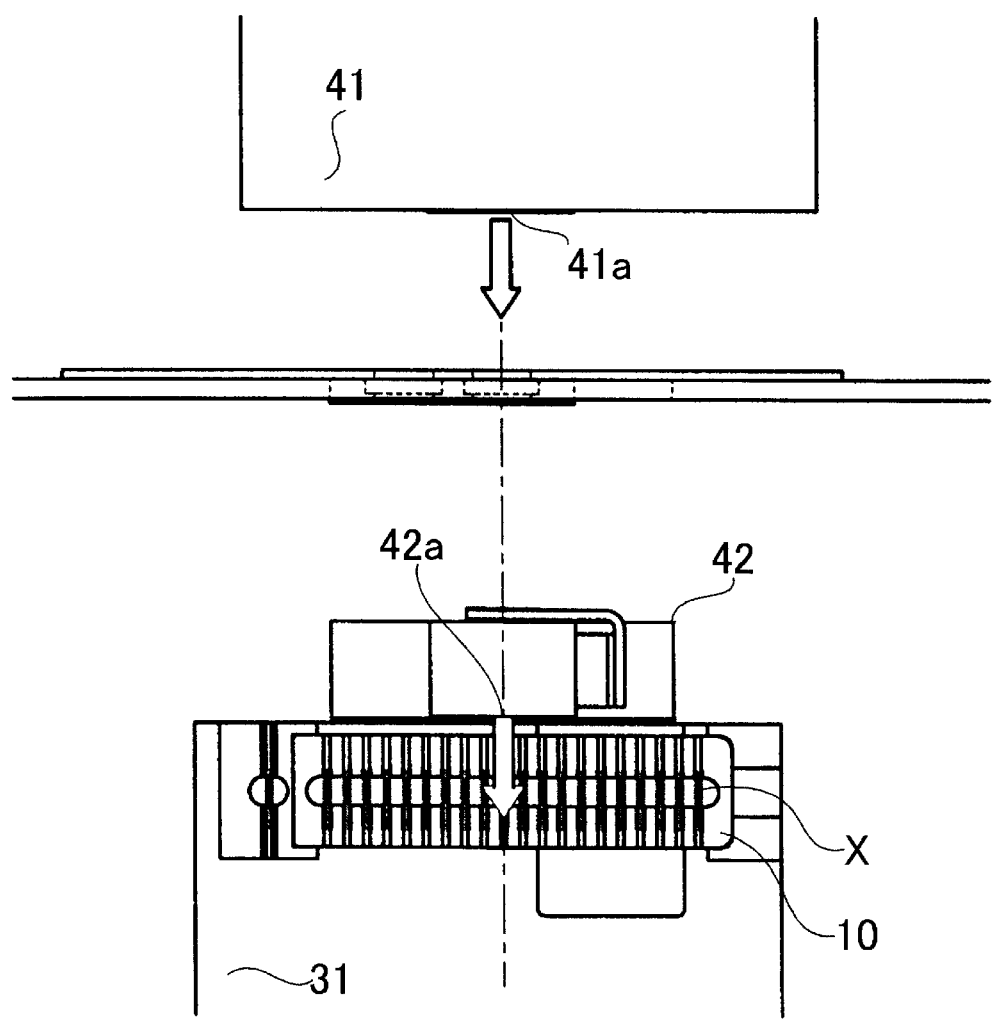
FIG. 7 is a plan view showing an ultraviolet irradiation path in the embodiment in FIG. 2.

The ultraviolet irradiating section 40 is constituted by a laser oscillator 41 disposed in the upper portion of the case section 21 and a reference unit 42. The laser oscillator 41 is an lasing device which emits an ultraviolet laser beam at a prescribed wavelength, for which a device such as a nitrogen gas laser, or the like, may be used, for example. As shown in FIG. 7, a first slit plate 41a having a slit hole for controlling the emitted light is installed on the laser beam emission window in the laser oscillator 41. The size of the slit hole formed in this first slit plate 41a is smaller than the diameter of the fluorescent glass elements X, for example, it is a rectangular parallelepiped shape of 1.3×10 mm.

Moreover, the reference unit 42 is provided in a position corresponding to the passage of the laser beam from the laser oscillator 41 to the fluorescent glass elements X, and a half mirror is provided for splitting the light exciting the reference glass provided inside the reference unit 42, in order to correct output variations in the laser oscillator 41. In this reference unit 42, a second slit plate 42a comprising a slit hole for controlling the incident light is provided on the fluorescent glass element X side thereof at the position of passage of the laser beam. The size of the slit hole formed in the second slit plate 42a can be taken to be 3 mm in diameter, for example.

(A-1-5) Fluorescence Detecting Section

As illustrated in FIG. 6, the fluorescence detecting section 50 comprises an photomultiplier tube 51 forming a fluorescence detecting element, and a hemispherical lens 52. This photomultiplier tube 51 converts fluorescence from the fluorescent glass elements X into an electrical signal, and the hemispherical lens 52 condenses the fluorescence from the fluorescent glass elements X, and inputs it to the photomultiplier tube 51. If appropriate, an optical filter for selectively transmitting a prescribed wavelength is positioned in the path of the laser beam and the fluorescence in the aforementioned ultraviolet irradiating section 40 and fluorescence detecting section 50, but description thereof is omitted here.

(A-2) Action

Dose reading using the dose reading device according to the present embodiment having the composition described above is performed in the following manner.

Namely, as illustrated in FIG. 3, the door cover 23a is opened, a magazine 10 accommodating a plurality of fluorescent glass elements X which are to be measured is set in the holders 31a of the moving table 31, and the door cover 23a is closed. Next, the direct drive unit 32 is driven, and the moving table 31 is moved until the fluorescent glass element X in the magazine 10 that is to be measured first arrives at a fluorescence detection position. Thereupon, an ultraviolet laser beam is emitted from the laser oscillator 41 onto this fluorescent glass element X that is to be measured.

Figure 8:
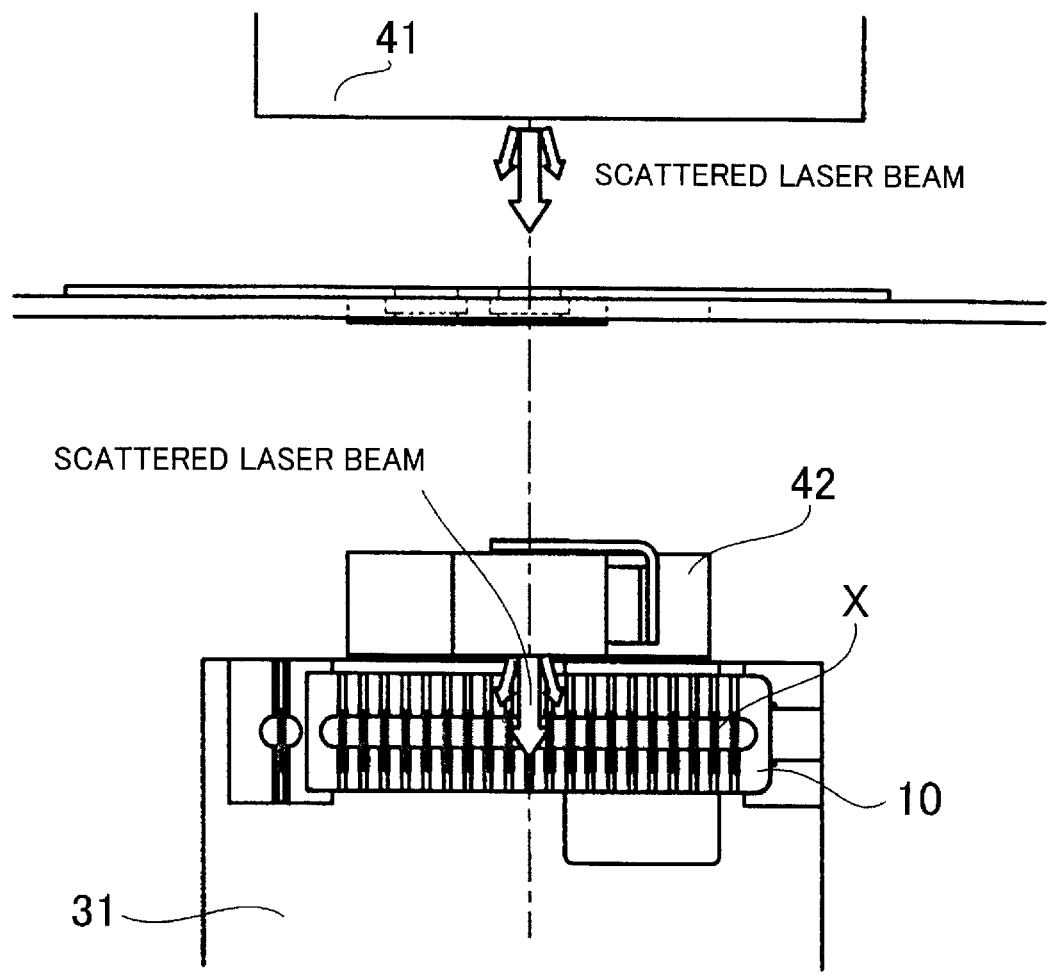
FIG. 8 is a plan view showing an ultraviolet irradiation path in a case where no slit plate is provided.

When using a nitrogen gas laser, for example, this ultraviolet laser beam does not form a complete parallel beam, but rather enlarges and disperses slightly, as illustrated by the example shown in FIG. 8 where the first slit plate 41a is not provided. However, in the dose reading device according to the present embodiment, a first slit 41a is provided in the emission window of the laser oscillator 41, as illustrated in FIG. 7, and hence enlargement and dispersion of the ultraviolet laser beam is prevented. In particular, when the lateral width of the slit hole is taken as 1.3 mm, then an optimum laser spot diameter that is not liable to be incident on adjacent fluorescent glass elements X is achieved for 1.5 mm diameter fluorescent glass elements.

The ultraviolet laser beam transmitted through the first slit plate 41a passes through a diaphragm (not illustrated) having an aperture of 1 mm diameter, for example, provided directly in front of the reference unit 42, whereby the effective sectional shape of the laser beam incident on the fluorescent glass element X in the reference unit 42 is regulated, and then enters the reference unit 42.

Furthermore, the ultraviolet laser beam having passed through the reference unit 42 then passes through the cutaway section 12 of the magazine 10 and is incident on the fluorescent glass element X to be measured. The fluorescent glass element X is excited by the ultraviolet laser beam incident thereon, and generates fluorescence that is directly proportional to its exposure dose. As shown in FIG. 6, this fluorescence passes through the aperture window 13 of the magazine 10 and the fluorescence transmission window 31d of the moving table 31, is condensed by the hemispherical lens 52, and is detected by the photomultiplier tube 51.

The reference unit 42 corrects variations in the output of the laser oscillator 41 on the basis of the ultraviolet laser beam split by the half mirror, but as shown in FIG. 8, if there is no second slit plate 42a, then there is a possibility that the scattered light generated thereby will become incident on the adjacent fluorescent glass elements X. However, in the dose reading device according to the present embodiment, incidence of scattered light onto the adjacent fluorescent glass elements X is prevented by passing the ultraviolet laser beam through a slit hole formed in the second slit plate 42a, as shown in FIG. 7.

However, in some cases, the fluorescent glass elements X adjacent to the element under measurement may be excited by very slight scattering of ultraviolet radiation and produce a small amount of fluorescence. Nevertheless, as shown in FIG. 6, the fluorescence generated by these adjacent fluorescent glass elements X is shielded by the second shield pate 31e, and hence only the fluorescence from the fluorescent glass element X being measured is detected by the photomultiplier tube 51.

More specifically, in the case of a dose reading device having a measurable range of 1 $\mu$Gy (Sv)–10 Gy (Sv), in the absence of a second shielding plate 31e, supposing that the fluorescent glass element X under measurement has an exposure dose of 10 $\mu$Gy (Sv) and an adjacent fluorescent glass element X has an exposure dose of 1 Gy (Sv), then even if scattered light having 1/100,000 the intensity of the exciting ultraviolet radiation is incident on the adjacent element, fluorescence corresponding to 10 $\mu$Gy (Sv) will be generated thereby and if this fluorescence is incident on the photomultiplier tube 51, then the measurement accuracy for the fluorescent glass element X under measurement will be significantly degraded. However, in the dose reading device according to the present embodiment, the second shielding plate 31e shields this surplus fluorescence and hence high measurement accuracy can be maintained.

On the other hand, since the ultraviolet laser beam transmitted through the fluorescent glass element X is not in fact completely absorbed by the interior walls of the dark box, some slight reflected light occurs. If this reflected light is incident on the fluorescent glass elements X other than the element under measurement, then the fluorescence generated thereby will interfere with the fluorescence from the fluorescent glass element X under measurement, hence degrading the reliability of the measurement value. However, in the dose reading device according to the present embodiment, the ultraviolet laser beam passing through the fluorescent glass element X is changed to a non-perpendicular direction upon striking the first shielding plate 31c, and therefore it does not return to the fluorescent glass elements X accommodated in the magazine 10. Therefore, only the fluorescence from the fluorescent glass element X under measurement is detected by the photomultiplier tube 51.

(A-3) Merits

The merits of the dose reading device according to the present embodiment described above are as follows. Namely, since the magazine conveying section 30, and both the position for ultraviolet irradiation by the ultraviolet irradiation section 40 and the position for fluorescence detection by the fluorescence detecting section 50, are located inside a dark box constituted inside the front cover 23, it is possible to perform dose reading without extracting the fluorescent glass elements X from the magazine 10. Consequently, no time is taken for the task of conveying the fluorescent glass elements X to the measurement position, and furthermore, conveyance problems, and deterioration of the fluorescence-based measurement accuracy caused by consequent breaking, soiling or foreign matter contamination of the fluorescent glass, are not liable to occur.

In particular, since the magazine conveying section 30 is only required to move the magazine in one direction, the mechanism is simple and the device can be compactified, and furthermore, the small-sized fluorescent glass elements X can readily be registered in position accurately. Moreover, since the reading operation for a plurality of fluorescent glass elements X can be performed continuously while moving the magazine 10 in progressive fashion, it is possible significantly to shorten the reading time. Furthermore, since no mechanism is required to extract the fluorescent glass elements X the manufacturing costs can be reduced and the overall device can be compactified.

Since the ultraviolet laser beam generated by the laser oscillator 41 is prevented from scattering by the slit plates 41a, 42a when it is incident on the fluorescent glass element X under measurement, it is possible to prevent virtually any generation of surplus fluorescence by incidence of the laser beam on other fluorescent glass elements X. Even if fluorescence is generated by a fluorescent glass element X other than the element under measurement due to partially scattered ultraviolet light, this surplus fluorescence is shielded by the second shielding plate 31e. Moreover, the ultraviolet laser beam having passed through the fluorescent glass element X under measurement is not reflected normally by the first shielding plate 31c, and is hence prevented from returning towards the magazine 10, thereby preventing further generation of surplus fluorescence. Consequently, it is possible reliably to detect only the fluorescence from the fluorescent glass element X under measurement, and hence accurate radiation dose reading can be achieved.

(A-4) Other Embodiments

The present invention is not limited to the embodiment described above, and may be modified appropriately in terms of the size, shape, number, material and type of the respective members, and the like. For example, the irradiating means is not limited to a nitrogen gas laser and another type of laser generating device, or the like, may be used, provided that it can irradiate ultraviolet light for exciting the fluorescent glasses. Moreover, the detecting means is not limited to that illustrated in relation to the foregoing embodiment, provided that it is capable of detecting the quantity of fluorescence. For example, it is not strictly necessary to use a hemispherical lens for condensing the fluorescence, and an aspherical lens may be used for this. Means for condensing the fluorescence may also be omitted.

The magazine conveying means may also be designed freely with regard to structure, conveyance direction, conveyance distance, and the like, provided that it is capable of sequentially conveying the fluorescent glass elements under measurement to a measurement position. The magazine may also be designed freely with regard to the structure thereof and the number of fluorescent glass elements accommodated therein, provided that it is capable of accommodating a plurality of fluorescent glass elements, in such a manner that ultraviolet irradiation and fluorescence detection can be performed while the fluorescent glass elements are accommodated therein. Moreover, the present invention may be implemented by a variety of embodiments, by combining the respective claims of the invention; for example, it may be implemented in such a manner that the shielding plates and slit plates in the foregoing embodiment are partially or wholly omitted.

[B. Dose Reading Magazine]

(B-1) Composition of the Dose Reading Magazine

Figure 9:
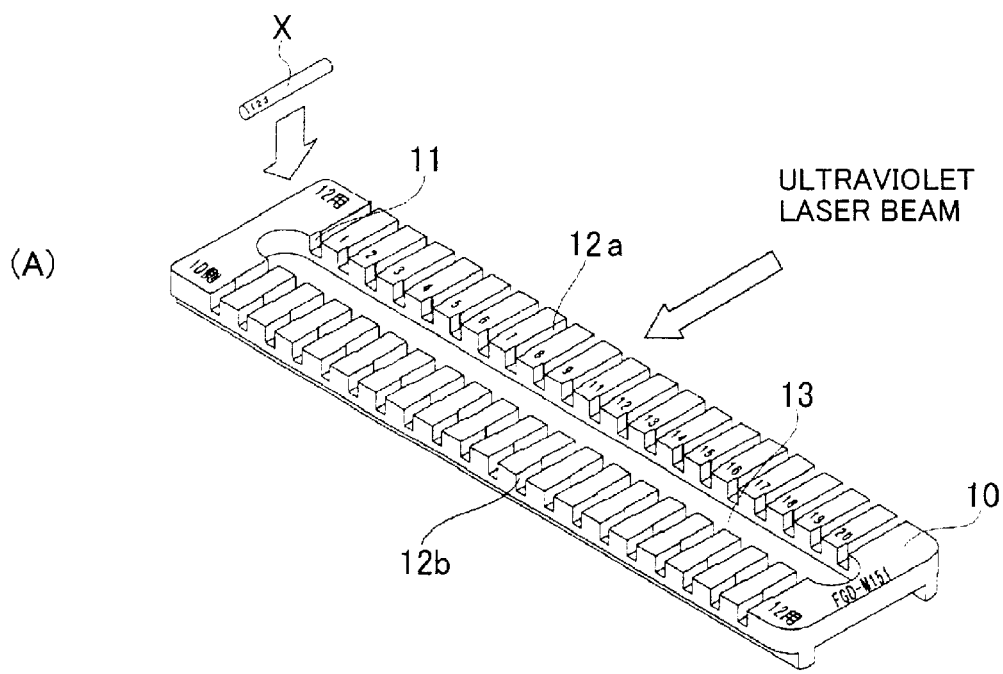
FIG. 9 is a diagram showing the composition of a dose reading magazine relating to the present invention.
Figure 9:
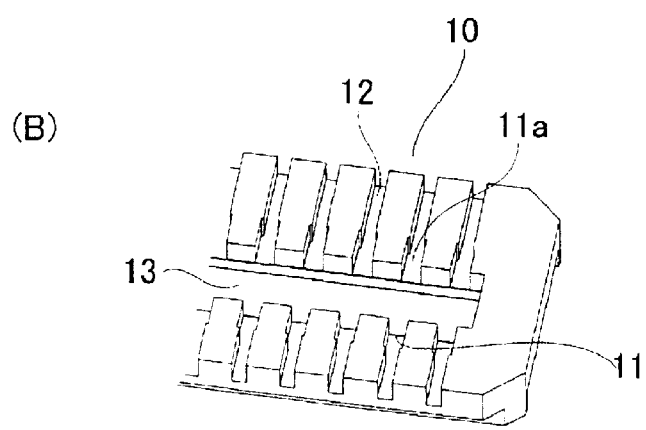

As illustrated in FIG. 9(A), the dose reading magazine 10 according to the present embodiment is made of black ABS (Acrylonitrile Butadiene Styrene) resin and has a thin rectangular parallelepiped shape, and incorporates twenty loading sections 11 for loading the fluorescent glass elements X, disposed in parallel fashion to the shorter edges thereof. As shown in FIG. 9(B), recess-shaped grooves 11a for holding either end of a fluorescent glass element X are formed in each loading section 11. Furthermore, cutaway sections 12a, 12b forming respective light paths are formed on the line of extension of the longitudinal axis of each respective loading section 11, in order that an ultraviolet laser beam can enter and exit therethrough. Identification numbers from 1 to 20 are attached to these loading sections 11.

The cutaway section 12a on the incident side is set to a greater width than that of the incident ultraviolet laser beam. For example, in the case that the ultraviolet laser beam is limited by a slit hole, or the like, then it is set to a width greater than the width of this slit. This is because if it is sought to use the magazine for the slit function for limiting the incident laser light incident, then variations in measurement accuracy will arise, since it is not possible to achieve uniform size of the slit sections in each cutaway section, due to fabrication accuracy problems.

Furthermore, as described in Japanese Patent No. 3,057,168, in order to correct the output variation of the ultraviolet laser, it is possible to monitor the ultraviolet light intensity by splitting the ultraviolet laser beam after it has passed through a slit hole, or the like, and directing it to a reference unit, but if a slit function is imparted to the magazine, then it is difficult to ensure that the laser spot incident on the fluorescent glass element X and the laser spot incident on the reference unit will be the same.

Furthermore, cutaway section 12b on the output side is set so as to allow the laser light that has passed through the glass element to exit without alteration. If no cutaways are provided in this section and the light path is shielded, then unattenuated laser light will be reflected and scattered, and become incident on adjacent glass elements, thereby giving rise to problems such as interference of fluorescence from adjacent elements.

Moreover, an aperture window 13 which spans the plurality of fluorescent glass elements X is provided in the base side of the magazine 10, in such a manner that it transects the central portions of the fluorescent glass elements X held in the loading section 11. This aperture window 13 eliminates the effects of light reflection from the end faces, in order to function as a fluorescence detection hole, and it is formed continuously and integrally in the longitudinal direction of the magazine 10, in order that the fluorescent glass elements X can be held readily. This aperture window 13 can also be formed individually for each respective loading section 11, but in this case, desirably, the respective aperture windows 13 are formed so as to have a uniform area, in order to prevent variations in measurement accuracy. Incidentally, for the fluorescent glass elements X accommodated in the magazine 10 described above, it is possible to use, for example, small-sized elements having a diameter of approximately 1.5 mm.

(B-2) Material of Dose Reading Magazine

As a result of varied and thorough research into materials for a dose reading magazine having the composition described above, the present inventors discovered that ABS (Acrylonitrile Butadiene Styrene) resin is the most suitable.

More specifically, in the prior art, a stainless steel metal frame comprising holding cords for holding individual glass elements has been used, but although this is advantageous in that the metal, such as stainless steel, or the like, does not generate fluorescence when irradiated with ultraviolet radiation, in a magazine wherein a multiplicity of fluorescent glass elements are loaded, such as the dose reading magazine relating to the present invention, it is necessary to provide treatment for eliminating surface reflectance, in order to prevent dispersed or scattered light from the ultraviolet laser beam from being incident on adjacent fluorescent glass elements, in addition to which, there are problems relating to moldability and cost.

Therefore, dose reading magazines were fabricated using the various resins listed in Table 1, similar glass elements were loaded therein, and the amount of fluorescence generated upon irradiation thereof by ultraviolet light was investigated, the corresponding results being indicated in Table 1.

TABLE 1

| MATERIAL | INTENSITY OF FLUORESCENCE ($\mu$Gy) | INCREMENT ($\mu$Gy) |
| --- | --- | --- |
| STAINLESS STEEL (STANDARD) | 72 | — |
| ABS (Acrylonitrile Butadiene Styrene, Black) | 68 | — |
| PET (Polyethylene Terephthalate) | 171 | 99 |
| PP (Polypropylene) | 115 | 43 |
| PC (Polycarbonate) | 254 | 182 |

As this table reveals, ABS resin produces virtually no fluorescence, similarly to stainless steel. Moreover, desirably, black ABS resin is used, in order to prevent generation of fluorescence from adjacent elements, due to reflection and scattering of the excitation light.

(B-3) Application Example of Dose Reading Magazine

Below, an overview is described of a case where a dose reading magazine having the aforementioned composition is used in a dose reading device such as that described in [A. Dose reading device] above.

Figure 10:
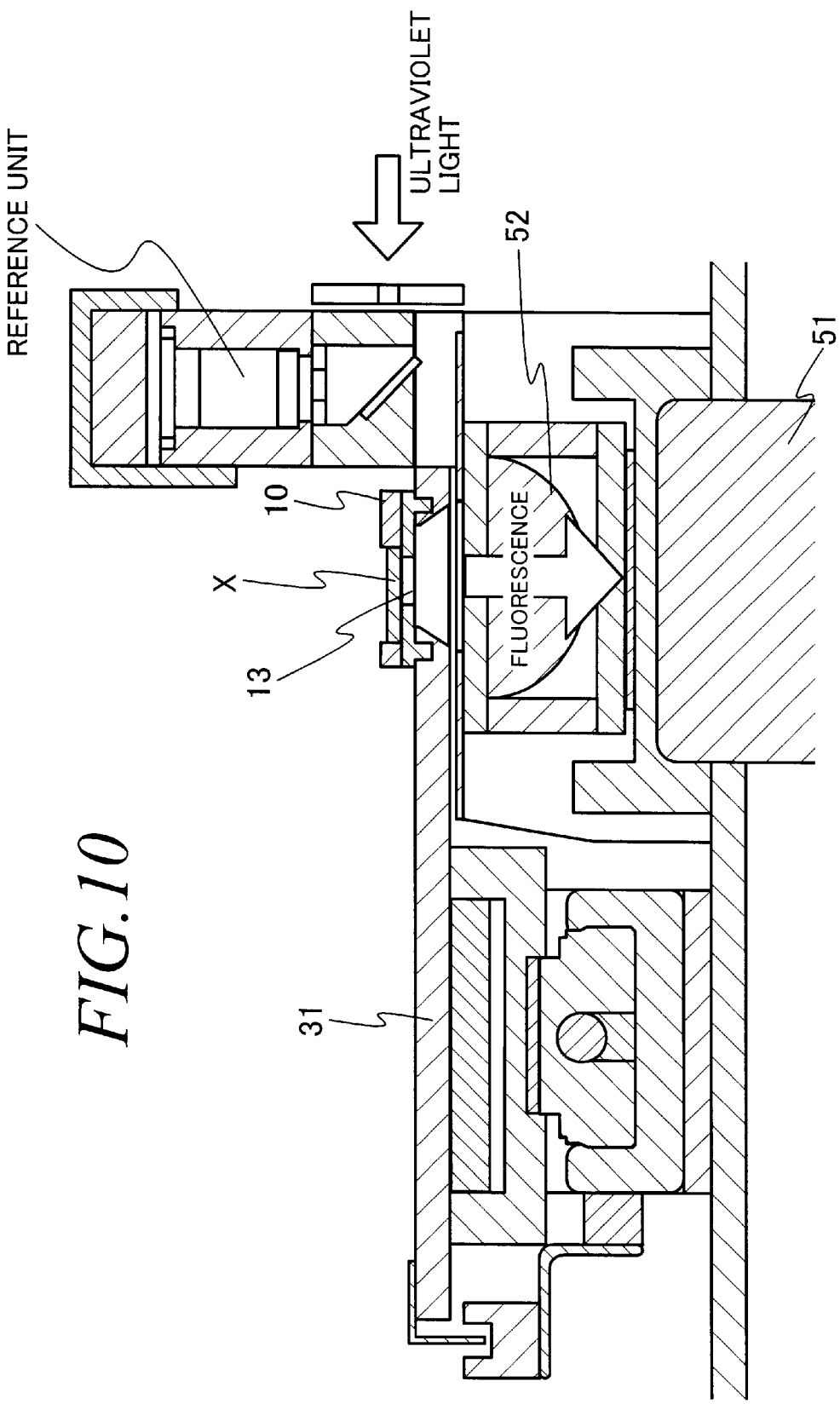
FIG. 10 is a side view showing one example of a dose reading device using a dose reading magazine relating to the present invention.

Specifically, the dose reading magazine according to the present embodiment has a composition whereby, as shown in FIG. 3, the door cover 23a provided in the dose reading device is opened, the magazine 10 holding a plurality of fluorescent glass elements to be measured is set in the holders 31a of the moving table 31, and the door cover 23a is closed, whereupon, as shown in FIG. 10, ultraviolet light is irradiated in the longitudinal direction of the fluorescent glass elements. This section forms a dark box. Moreover, a composition is adopted wherein the fluorescence generated by the fluorescent glass elements is detected via a condensing hemispherical lens 52, by an photomultiplier tube 51 which forms a fluorescence detecting element.

(B-4) Method of Manufacturing Magazine

Figure 11:
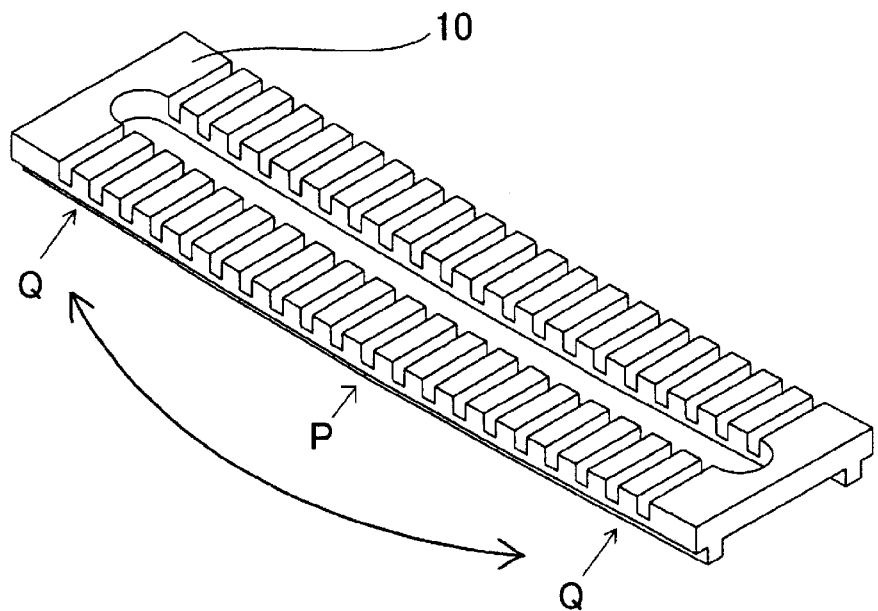
FIG. 11 is a perspective view showing a state where both end portions of a dose reading magazine are warped upwards.

Next, a method of manufacturing the magazine 10 is described. Specifically, when a magazine of the foregoing shape is formed from ABS, or another such resin, the magazine assumes an upwardly curved dish shape of large surface area, as illustrated in FIG. 11. For example, between the base portion of this dish shape (in the vicinity of point P in the diagram) and the end portions thereof (in the vicinity of points Q in the diagram), there is a height differential of approximately 0.1–0.5 mm in the face on which the fluorescent glass elements X are placed. This warp will give rise to differences in the point of incidence of the ultraviolet laser beam on the fluorescent glass elements X loaded in each respective loading section 11, and due to the effects of the lens efficiency this will lead to significant variation in the dose reading accuracy, which must be corrected. For example, in the case of bar-shaped fluorescent glass elements X having a diameter of 1.5 mm, a height differential of 20 $\mu$m in the point of incidence of the ultraviolet laser beam will give rise to a 1% change in the reading value.

Figure 12:
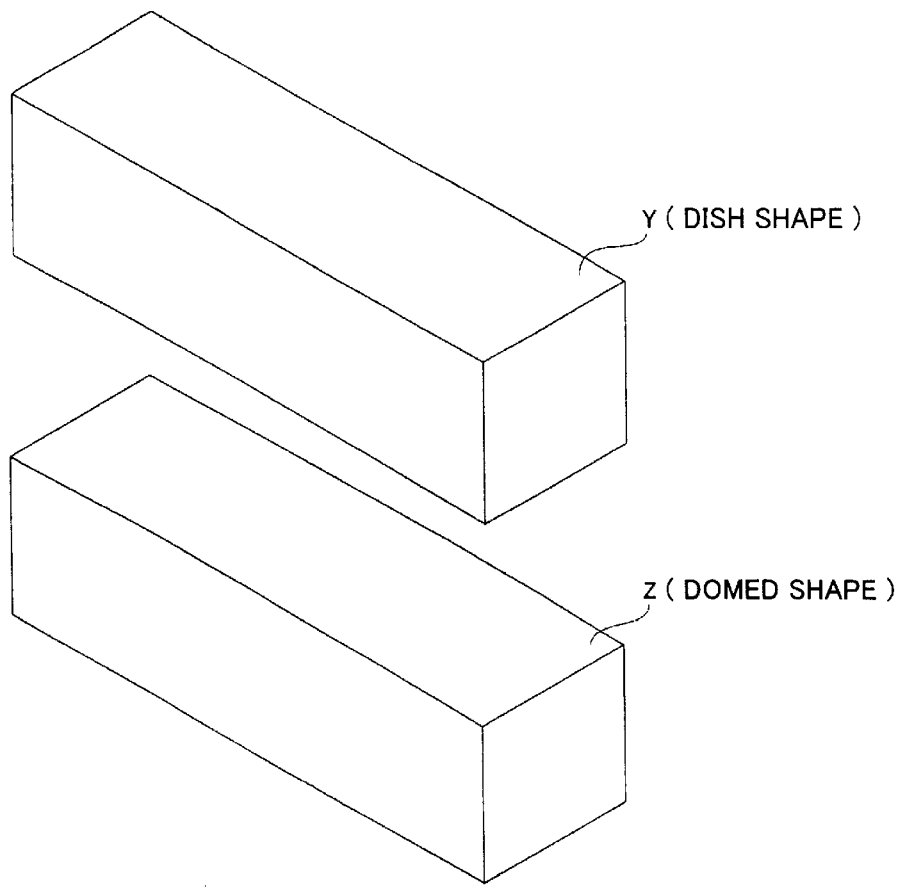
FIG. 12 is a perspective view showing correcting metal dies for a dose reading magazine.

Therefore, in the present embodiment, in order to correct a magazine warp of this kind, heating correction metal dies Y, Z are used, as illustrated in FIG. 12. More specifically, die Y situated above the magazine that is to undergo correction processing has a concave curved surface processed to a prescribed radius of curvature on the side thereof which contacts the magazine, while die Z situated below the magazine has a convex curved surface processed to a prescribed radius of curvature on the side thereof which contacts the magazine. This radius of curvature is, for example, taken as R 20,000.

Figure 13:
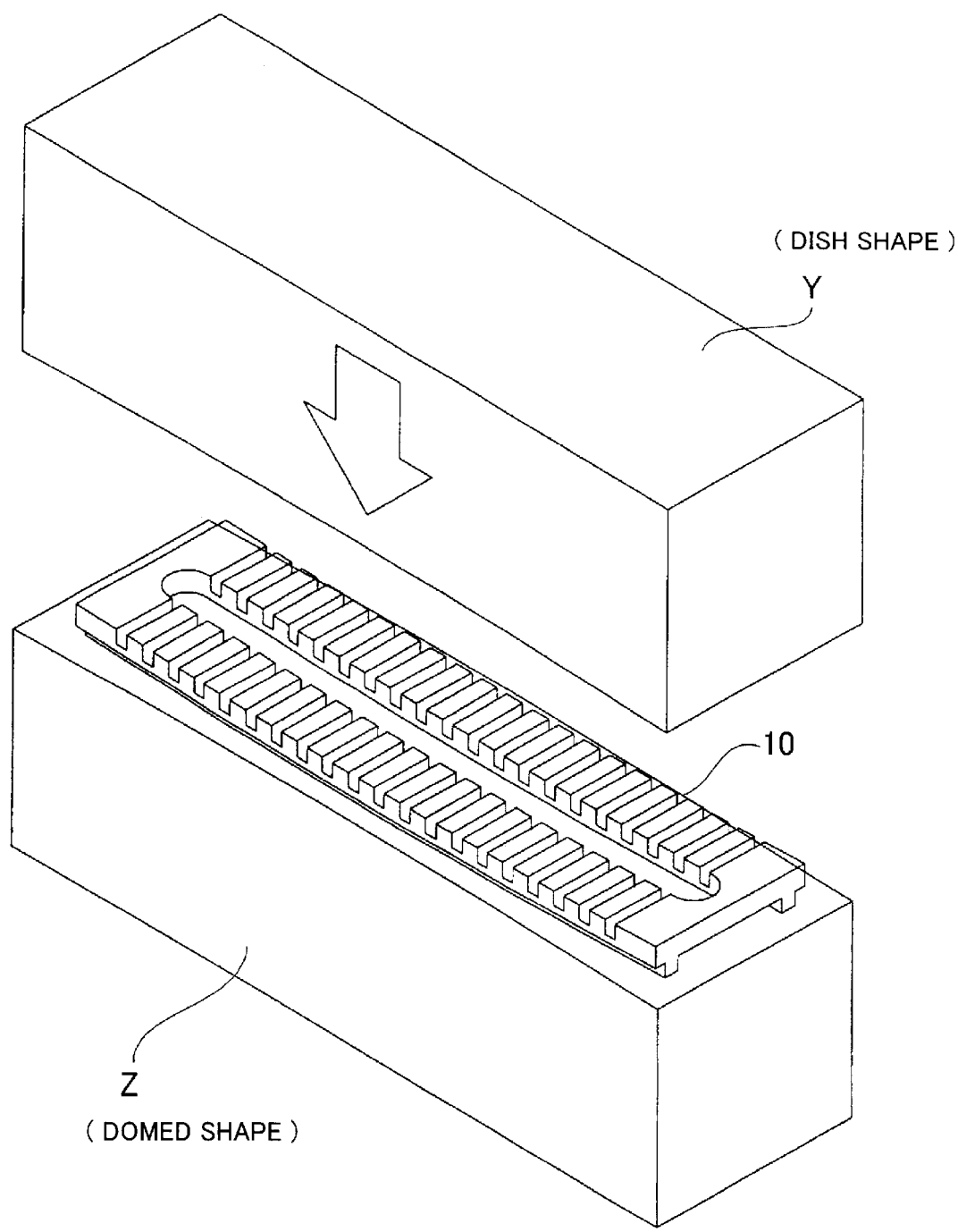
FIG. 13 is a perspective diagram showing a correction processing state for a dose reading magazine.

The procedure for correcting a warp of the magazine by means of these metal dies Y, Z is as follows. Namely, after molding, the magazine 10 is placed inbetween the dies Y, Z, as illustrated in FIG. 13. The magazine 10 held in this interposed state is then placed in a drier, where it is subjected to heat correction treatment for a prescribed period of time at a prescribed temperature. For example, a desirable heating temperature is 77° C., which is 3° C. lower than the loaded deflection temperature of the material. Moreover, the correction treatment time is desirably set in accordance with the amount of the warp, on the basis of the fact that the warp of the magazine 10 is corrected at a rate of 5 $\mu$m per minute. Immediately after this correction treatment, the magazine 10 assumes a domed shape according to its interposed state, but it returns to a flat shape in approximately 24 hours.

(B-5) Merits

According to the dose reading magazine of the present embodiment described above, since dose reading can be performed without extracting the fluorescent glass elements X from the magazine 10, no time is taken for the task of conveying the fluorescent glass elements X to the measurement position, and furthermore, conveyance problems, and deterioration of the fluorescence-based measurement accuracy caused by consequent breaking, soiling or foreign matter contamination of the fluorescent glass, are not liable to occur.

Moreover, when using the dose reading magazine according to the present embodiment, since the reading operation for a plurality of fluorescent glass elements X can be performed continuously while moving the magazine 10 in progressive fashion with the fluorescent glass elements accommodated therein, it is possible significantly to shorten the reading time. Furthermore, since no mechanism is required to extract the fluorescent glass elements X the manufacturing costs can be reduced and the overall device can be compactified. In particular, since the dose reading magazine according to the present embodiment has a structure whereby rod-shaped fluorescent glass elements X are held such that the axes thereof are mutually parallel, it is possible to compactify the dark box section of the magazine 10 and the dose reading device.

Moreover, since the aperture window 13 of the magazine 10 according to the present embodiment is formed integrally and continuously in the longitudinal direction of the magazine 10, it is possible to achieve accurate dose readings without variations caused by differences in the loading positions of the fluorescent glass elements X. Furthermore, although a fluorescent glass element X on which the ultraviolet laser beam is incident in the longitudinal axis direction thereof radiates fluorescence in the full circumferential direction thereof, since the aperture window 13 is formed integrally and continuously in the longitudinal direction of the magazine 10, the fluorescence emitted by the fluorescent glass element X is not restricted and is incident on a large area of the fluorescence detecting section, thereby yielding high sensitivity, compared to a case where separate aperture windows 13 are provided for each respective loading section 11.

Moreover, since the aperture window 13 is formed integrally and continuously in the longitudinal direction of the magazine 10, the fluorescent glass elements X can be grasped more readily, thereby facilitating installation and removal thereof, compared to a case where aperture windows 13 are provided individually for each loading section 11. If the aperture window is divided for each individual loading section 11, and a taper section is formed in the axial direction of the fluorescent glass elements X, then the interval between the fluorescent glass elements X increases, and it is no longer possible to mount a large number of fluorescent glass elements X, but since the aperture window 13 is formed continuously in the present embodiment, it is possible to mount a large number of fluorescent glass elements X, without increasing the interval between the respective fluorescent glass elements X.

Moreover, in the present embodiment, since the warp of the magazine 10 is corrected after molding by heating it by means of metal dies Y, Z, the warp is effectively eliminated and dose reading accuracy can be guaranteed, compared to cases adopting a method whereby the magazines are stacked together on trays after molding. For example, since the maximum height differential between the fluorescent glass element loading surfaces is approximately 10 μm after heat treatment, the variation in the reading value can be restricted to 1% or less. Moreover, since the warp is corrected by heating using metal dies Y, Z, the installation and removal of the magazine 10 poses no problem and the work bench is not required to have high strength, compared to cases where a mechanism is appended to the moving table 31 to press down and fix both ends of the magazine 10.

Moreover, the material of the magazine 10 in the present embodiment is ABS resin, which has been observed to produce virtually no fluorescence when subjected to irradiation of excitation ultraviolet light, compared to other resins, such as PS (polystyrene) and the like. Therefore, it is possible to achieve accurate readings, without interference to the fluorescence from the fluorescent glass element X under measurement. In particular, since the magazine 10 according to the present embodiment is black in colour, the generation of fluorescence from adjacent elements due to reflection or scattering of the excitation ultraviolet laser beam is prevented.

(B-6) Other Embodiments

The present invention is not limited to the embodiment described above, and may be modified appropriately in terms of the size, shape, number, material and type of the respective members, and the like. For example, the magazine may also be designed freely with regard to the structure thereof and the number of fluorescent glass elements accommodated therein, provided that it is capable of accommodating a plurality of fluorescent glass elements, in such a manner that ultraviolet irradiation and fluorescence detection can be performed while the fluorescent glass elements are accommodated therein. Any molding method suited to the resin may be used for molding the magazine, such as injection molding, compression, extrusion, variant extrusion, blowing, vacuum molding, and the like. Moreover, the magazine warp correcting method is not limited to the method using metal dies described above, provided that it corrects warp by heating while applying a load in the opposite direction to the warp. The amount of warp correction may also be set according to the desired dose reading accuracy, such that loading height of the fluorescent glass elements is standardized to a reference value.

Moreover, for the material of the magazine, it is possible to use other resins or materials other than resins, provided that they produce little or no fluorescence. Furthermore, the reading device to which the present invention is applied is not limited to that illustrated in the foregoing embodiment, provided that it is capable of irradiating ultraviolet light to excite the fluorescent glasses and detecting the amount of fluorescence.

[C. Dose Reading Device for High Doses]

(C-1) High Dose Reading Magazine (C-1-1) Composition

Firstly, the composition of the high dose reading magazine relating to the present invention is described. This high dose reading magazine is used for measurement of fluorescent glass elements that have been exposed to a hose dose of radiation.

Figure 14:
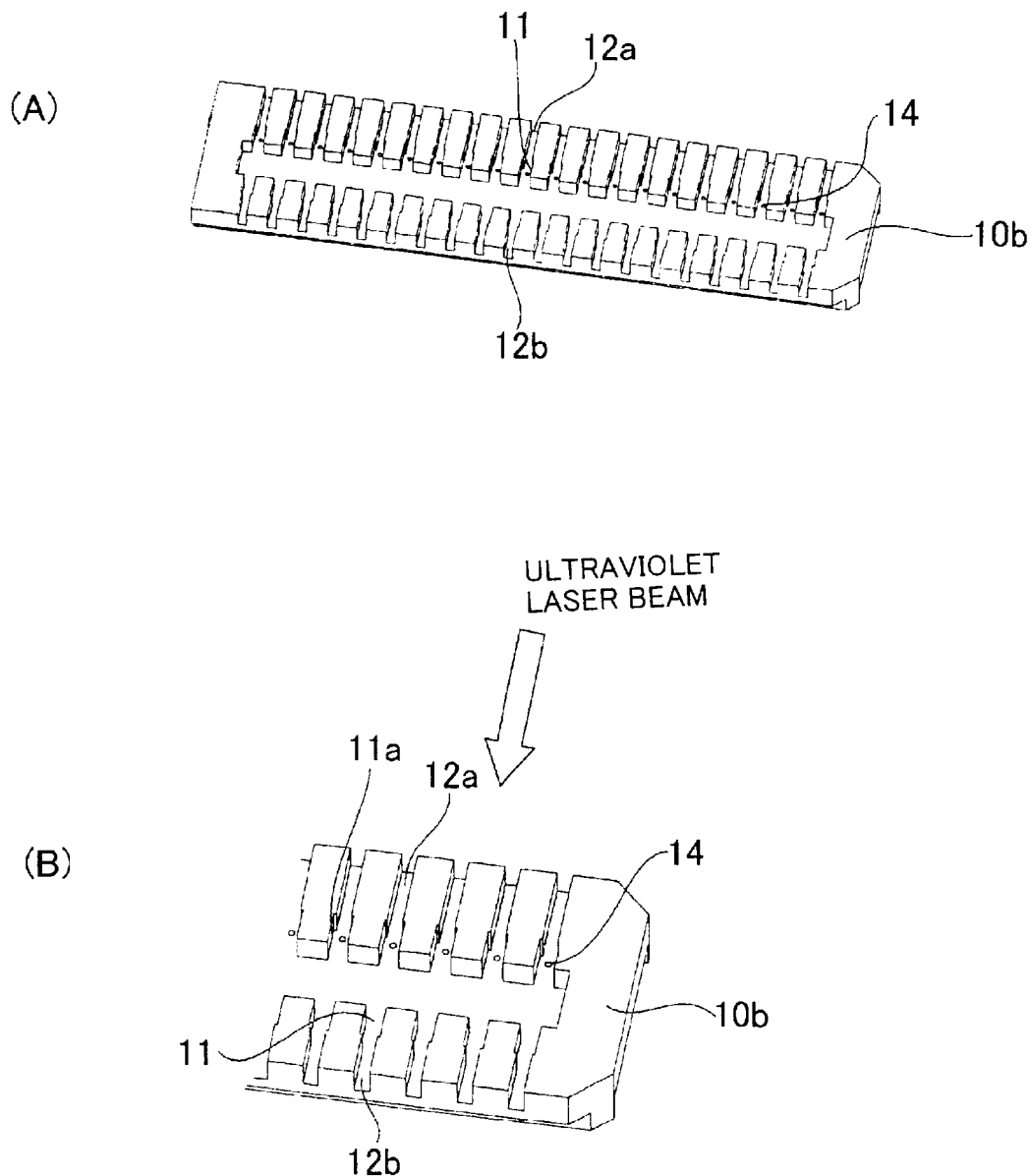
FIG. 14 is a diagram showing the composition of one embodiment of a high dose reading magazine relating to the present invention.

Specifically, the high dose reading magazine 10b according to the present embodiment is a black thin rectangular parallelepiped shape made from ABS (Acrylonitrile Butadiene Styrene) for example, as illustrated in FIG. 14(A), and incorporates twenty loading sections 11 for loading the fluorescent glass elements X, disposed in parallel fashion to the shorter edges thereof. As shown in FIG. 14(B), recess-shaped grooves 11a for holding either end of a fluorescent glass element X are formed in each loading section 11. Furthermore, cutaway sections 12a, 12b forming respective light paths are formed on the line of extension of the longitudinal axis of each respective loading section 11, in order that an ultraviolet laser beam can enter and exit therethrough. Identification numbers from 1 to 20 are attached to these loading sections 11.

Furthermore, as illustrated in FIG. 14(B), aperture holes 14 are formed in the base of the high dose reading magazine 10b, in the vicinity of the end portion of each loading section 11 on the side where the ultraviolet light is incident on the fluorescent glass element X. In the present embodiment, the sectional shape of the aperture holes 14 is tapered such that they broaden in the exit direction of the fluorescence. The aperture holes 14 are, for example, a hole having a diameter of approximately 0.6 mm.

The cutaway section 12a on the incident side is set to a greater width than that of the incident ultraviolet laser beam.

For example, in the case that the ultraviolet laser beam is limited by a slit hole, or the like, then it is set to a width greater than the width of this slit. This is because if it is sought to use the magazine for the slit function for limiting the incident laser light incident, then variations in measurement accuracy will arise, since it is not possible to achieve uniform size of the slit sections in each cutaway section, due to fabrication accuracy problems.

Furthermore, as described in Japanese Patent No. 3,057,168, in order to correct the output variation of the ultraviolet laser, it is possible to monitor the ultraviolet light intensity by splitting the ultraviolet laser beam after it has passed through a slit hole, or the like, and directing it to a reference unit, but if a slit function is imparted to the magazine, then it is difficult to ensure that the laser spot incident on the fluorescent glass element X and the laser spot incident on the reference unit will be the same.

Furthermore, cutaway section 12b on the output side is set so as to allow the laser light that has passed through the glass element to exit without alteration. If no cutaways are provided in this section and the light path is shielded, then unattenuated laser light will be reflected and scattered, and become incident on adjacent glass elements, thereby giving rise to problems such as interference of fluorescence from adjacent elements.

Figure 15:
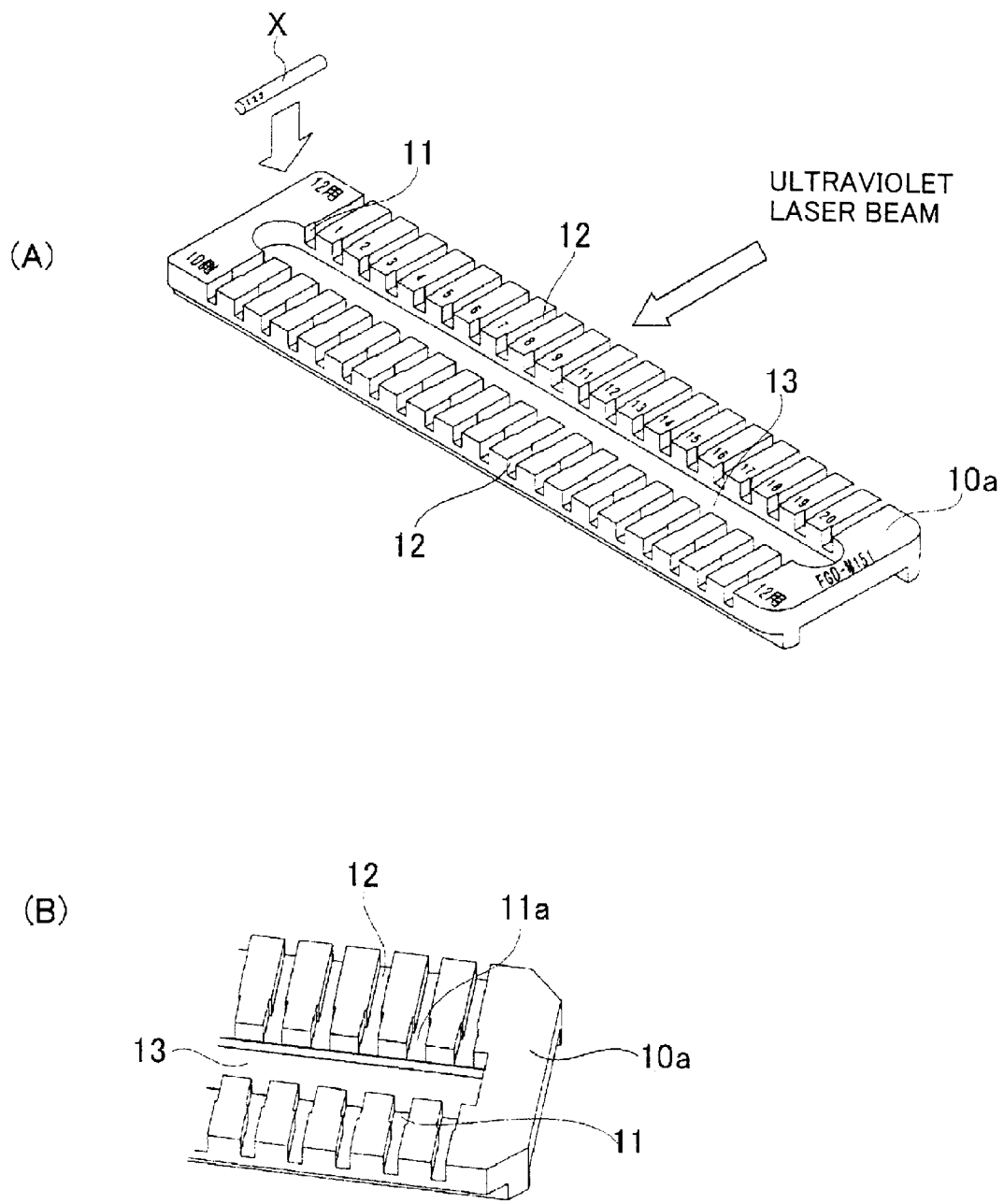
FIG. 15 is a diagram showing the composition of a normal dose reading magazine.

By contrast, a dose reading magazine used for standard radiation exposure doses (hereinafter, called normal dose reading magazine,) has a similar basic composition to that of the high dose magazine described above, as indicated in the aforementioned section [B. Dose reading magazine], but it is different in the following respect. Namely, as shown in FIG. 15(A) and (B), in a normal dose reading magazine 10a, an aperture window 13 which spans the plurality of fluorescent glass elements X is provided in the base side of the magazine 10a, in such a manner that it transects the central portions of the fluorescent glass elements X held in the loading section 11. This aperture window 13 eliminates the effects of light reflection from the end faces, in order to function as a fluorescence detection hole, and it is formed continuously and integrally in the longitudinal direction of the normal dose reading magazine 10, in order that the fluorescent glass elements X can be held readily. Incidentally, for the fluorescent glass elements X accommodated in the magazine 10 described above, it is possible to use, for example, small-sized elements having a diameter of approximately 1.5 mm.

(C-1-2) Action and Merits

The following action and merits can be obtained by means of the high dose reading magazine 10b according to the present embodiment.

Figure 16:
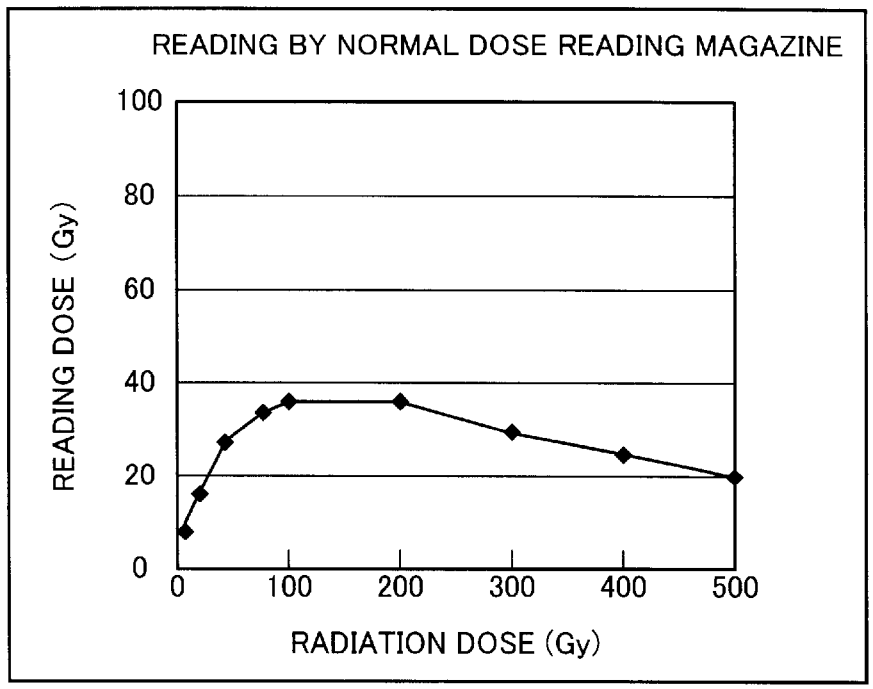
FIG. 16 is a graph showing dose in a case where high-dose reading is performed using a normal dose reading magazine.

Specifically, for the fluorescent glass elements X which have been irradiated with a high dose of radiation, the transmissivity of the ultraviolet laser beam is reduced with the increase in radiation dose, and hence the excitation ultraviolet light gradually becomes weaker as it progresses inside the glass, thereby reducing the intensity of the fluorescence generated. Consequently, for example, if a normal dose reading magazine 10a is used to read the fluorescence from a fluorescent glass element X that has been irradiated with a high dose of radiation, then as shown in FIG. 16, the reading value will start to decline at exposure doses of 100 Gy and above. Therefore, even with the same reading value, it will not be possible to distinguish whether or not the radiation dose is above 100 Gy, and furthermore, in the vicinity of 100 Gy, the reading value will not change even when the dose changes, meaning that the exposure dose cannot be measured accurately.

Figure 17:
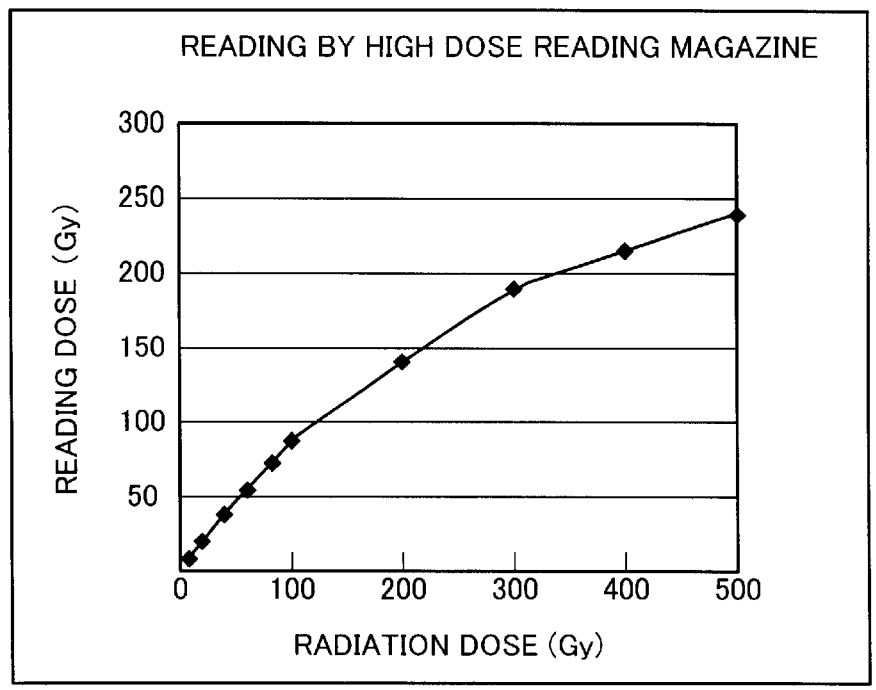
FIG. 17 is a graph showing dose in a case where high-dose reading is performed using a high dose reading magazine.

However, in the case of the high dose reading magazine 10b according to the present embodiment, since only the fluorescence from the end portion on the incident side of the ultraviolet laser beam is read, then as illustrated in FIG. 17, even at exposures of 100 Gy or above, the detected amount of fluorescence does not decline, but rather, increases steadily. Therefore, correction by means of a linear correction formula can be applied.

(C-2) Dose Reading Device (C-2-1) Composition of Dose Reading Device

Next, the composition of the dose reading device relating to the present invention is described. If appropriate, an optical filter for selectively transmitting a prescribed wavelength is positioned in the path of the ultraviolet laser beam (described below) and the fluorescence, but description thereof is omitted here.

Figure 18:
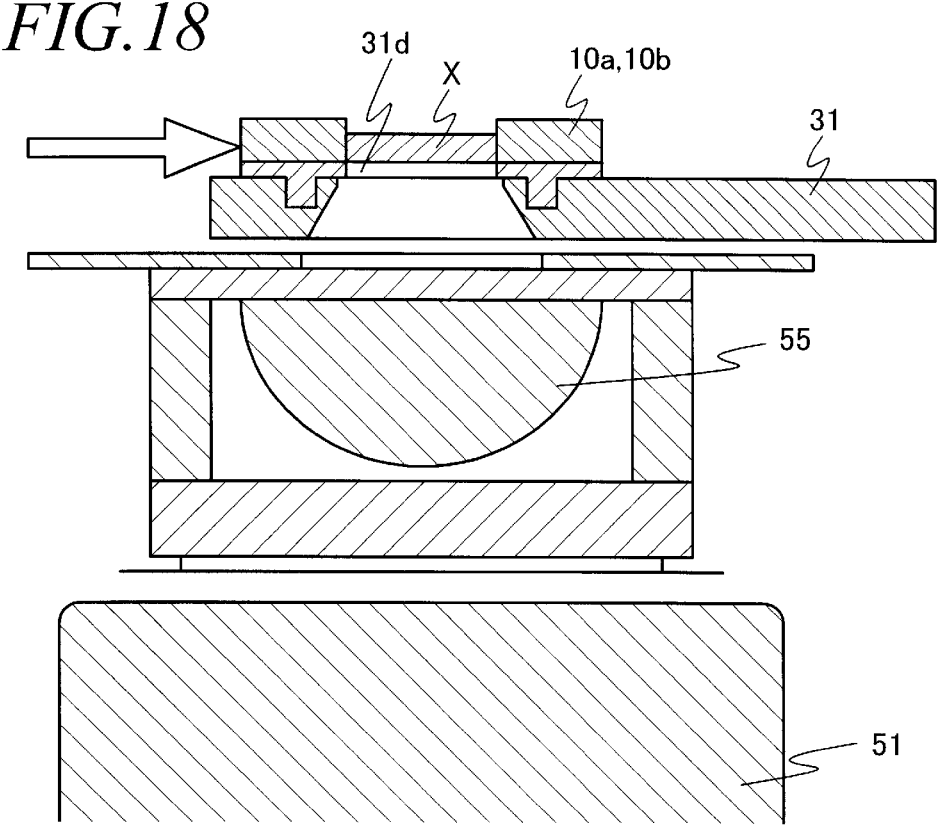
FIG. 18 is a vertical sectional view showing the composition of one embodiment of a dose reading device relating to the present invention.

Specifically, as shown in FIG. 18, the dose reading device according to the present embodiment comprises a moving table 31, ultraviolet irradiating section (not illustrated), condensing section 55, photomultiplier tube 51, and reflection type opto-electrical sensor (not illustrated). The moving table 31 is a table on which either of the two types of magazine, a normal dose reading magazine 10a or a high dose reading magazine 10b, is placed, provided in such a manner that it can be disposed in a fluorescence reading position by means of a magazine conveying device (not illustrated). Moreover, in this moving table 31, a fluorescence transmission window 31d for transmitting the fluorescence from the fluorescent glass element X is formed in a position corresponding to the aperture window 13 of the normal dose reading magazine 10a, or the aperture holes 14 of the high dose reading magazine 10b.

Moreover, although not shown in the diagrams, a calibration glass for calibrating the detection sensitivity of the photomultiplier tube 51 is provided on the moving table 31. The fluorescence exit window from this calibration glass is formed similarly to the aperture window 13 of the normal dose reading magazine 10a. For example, if the aperture window 13 is a slit having a width of 6 mm, then it is formed to the same width.

Furthermore, the condensing section 55 is provided in the lower portion of the moving table 31 at the fluorescence reading position, and it comprises means for condensing the fluorescence from the fluorescent glass element X. It is possible to use a hemispherical lens, for example, for this condensing section 55. The photomultiplier tube 51 comprises means for detecting the fluorescence condensed by the condensing section 55, by converting same to an electrical signal.

Figure 19:
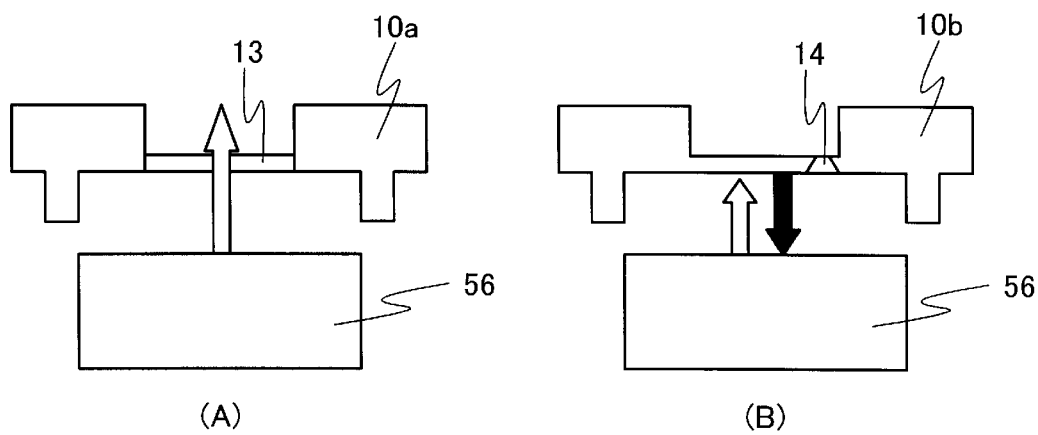
FIG. 19 is a diagram showing the principles of detecting the type of magazine in the dose reading device shown in FIG. 18.

Moreover, the reflection-type opto-electrical sensor 56 is fixed to the base in the lower portion of the moving table 31, and as shown in FIG. 19, it comprises means for detecting whether the magazine is either a normal dose reading magazine 10a or a high dose reading magazine 10b, on the basis of the amount of output light reflected by the under face of the magazine 10a or 10b set in the fluorescence reading position. In other words, since the normal dose reading magazine 10a has an aperture window 13 comprising a large aperture area, the amount of light reflected by the reflection-type opto-electrical sensor 56 is small, as illustrated interface FIG. 19(A). On the other hand, the high dose reading magazine 10b only comprises aperture holes 14, and therefore the amount of light reflected by the reflection-type opto-electrical sensor 56 will be high, as shown in FIG. 19(B). On the basis of this effect, it is possible to detect whether the fluorescent glass elements X to be measured are accommodated in a normal dose reading magazine 10a or a high dose reading magazine 10b.

Moreover, a dose reading processing section as described below is provided in the dose reading device according to the present embodiment. This dose reading processing section is composed such that it corrects the sensitivity of the photomultiplier tube 51, separately for normal reading mode cases and high reading mode cases, on the basis of the amount of fluorescence detected by the calibration glass. Furthermore, it is also composed such that, in calculating the exposure doses, the fluorescence reading values are corrected by respective linear correction formulas previously defined separately for normal reading mode cases (where the radiation exposure dose is 2 Gy or above) and high dose reading mode cases (where the radiation exposure dose is 20 Gy or above). Moreover, it is also composed such that the calculated exposure dose is displayed with respective units of "$\mu$Gy" or "mGy", for the normal reading mode and high reading mode.

(C-2-2) Composition of the Dose Reading Processing Section

The dose reading device according to the present embodiment and having the composition described above comprises a dose reading processing section having a composition of the following kind.

Figure 20:
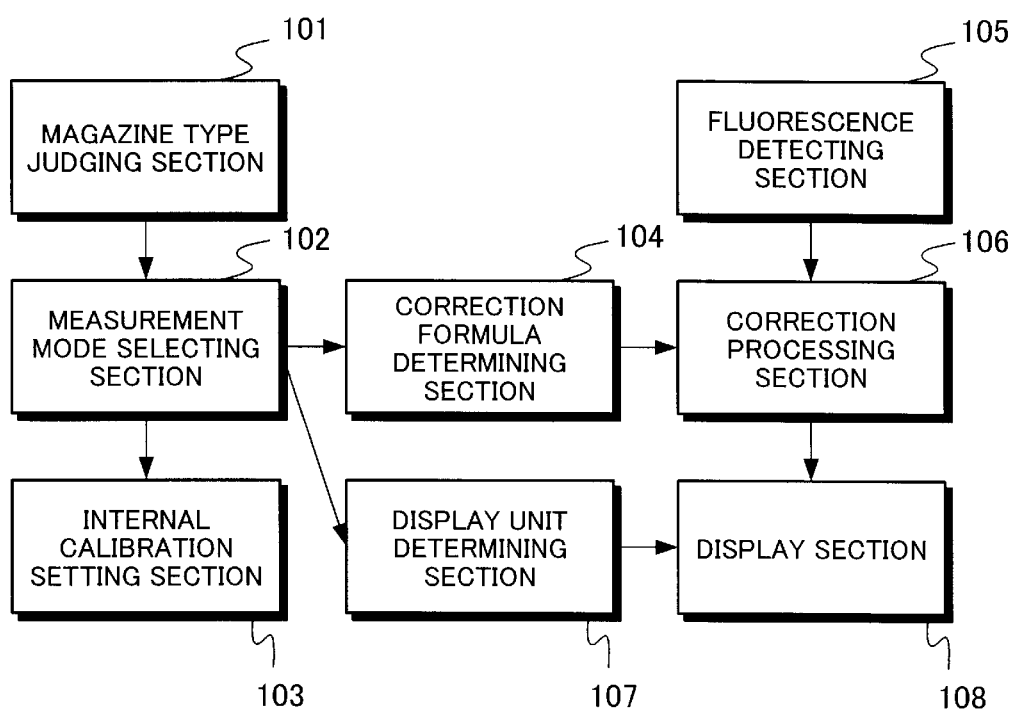
FIG. 20 is a functional block diagram showing the composition of a dose reading processing section of a dose reading device relating to the present invention.

Namely, as illustrated in FIG. 20, the dose reading processing section comprises a magazine type judging section 101 (for example, the aforementioned reflection type opto-electrical sensor 56) for judging whether the magazine located at the measurement point is a normal dose reading magazine or a high dose reading magazine; a measurement mode selecting section 102 for selecting a measurement mode on the basis of the judgement results of the magazine type determining section 101; an internal calibration setting section 103 for correcting the detection sensitivity of the photomultiplier tube 51 on the basis of the measurement mode selected by the measurement mode selection section 102; a correction formula determining section 104 for determining a correction formula to be applied, on the basis of the aforementioned measurement mode; a fluorescence detecting section 105 for measuring the fluorescence of the fluorescent glass element under measurement, by means of a prescribed fluorescence detecting element; a correction processing section 106 for correcting the amount of fluorescence detected by the fluorescence detecting section 105, on the basis of the aforementioned correction formula, a display unit determining section 107 for determining and displaying the display units, and a display section 108 for displaying the detection results.

A dose reading processing section of this kind is realized by means of a computer program.

(C-2-3) Action

Figure 21:
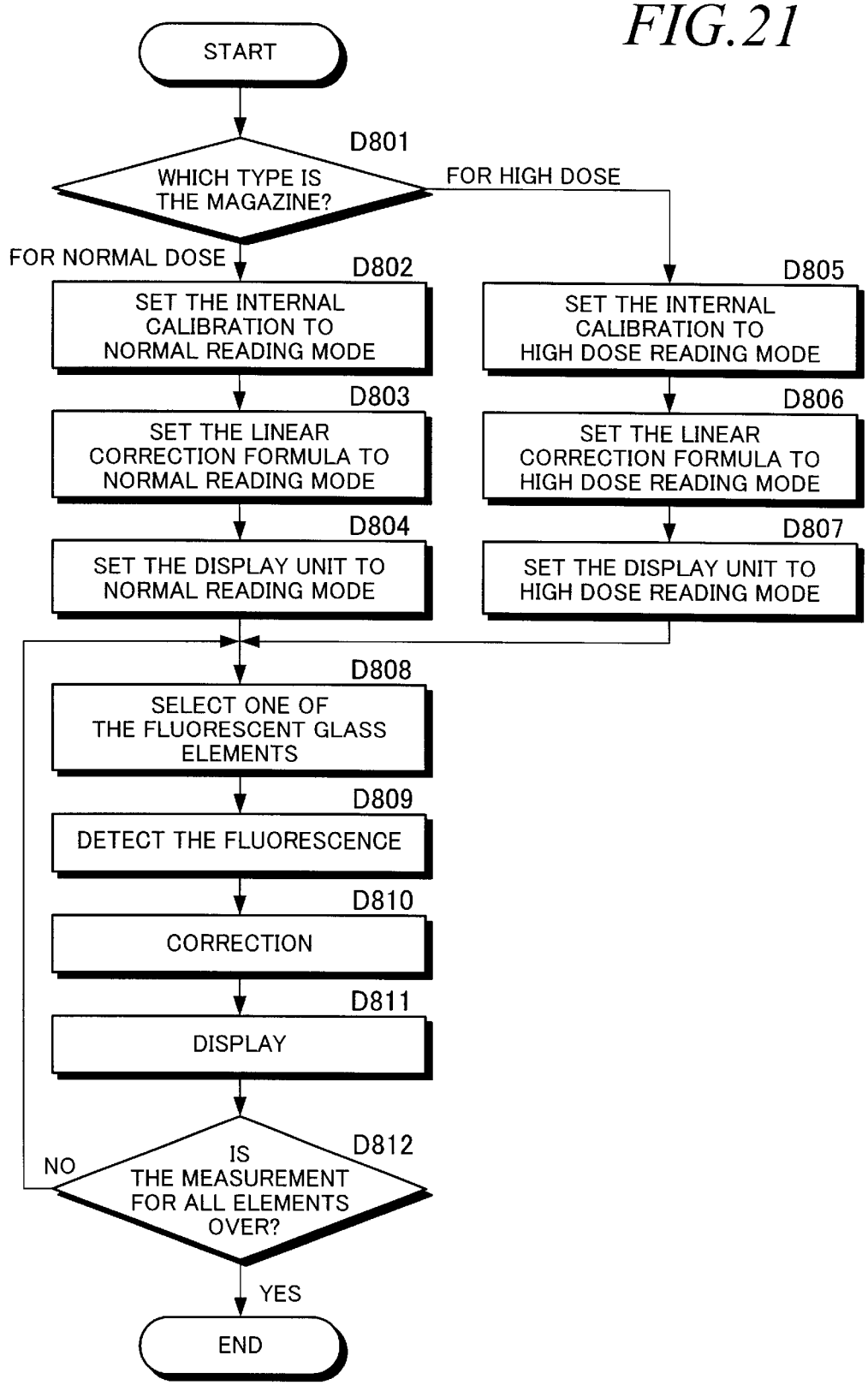
FIG. 21 is a flowchart showing a reading procedure in a dose reading processing section.

The procedure of dose reading processing by means of the dose reading device according to the present embodiment described above is explained here with reference to the flowchart in FIG. 21. Firstly, at step D801, the aforementioned reflection-type opto-electrical sensor 56 judges whether the magazine accommodating the fluorescent glass elements to be measured is a normal dose reading magazine or a high dose reading magazine. If it judges the magazine to be a normal dose reading magazine, then the internal calibration is set to "Standard" (step D802), the linear correction formula for the detection value is set to "Normal reading mode" (Step D803), and the displayed mode for the exposure dose is set to "Normal reading mode" (Step D804).

If, on the other hand, the magazine accommodating the fluorescent glass elements to be measured is judged to be a high dose reading magazine at step D801, then the internal calibration is set to "high dose" (Step D805), the linear correction formula for the detected value is set to "high dose mode" (step D806), and the exposure dose display mode is set to "high dose mode" (step D807).

Figure 22:
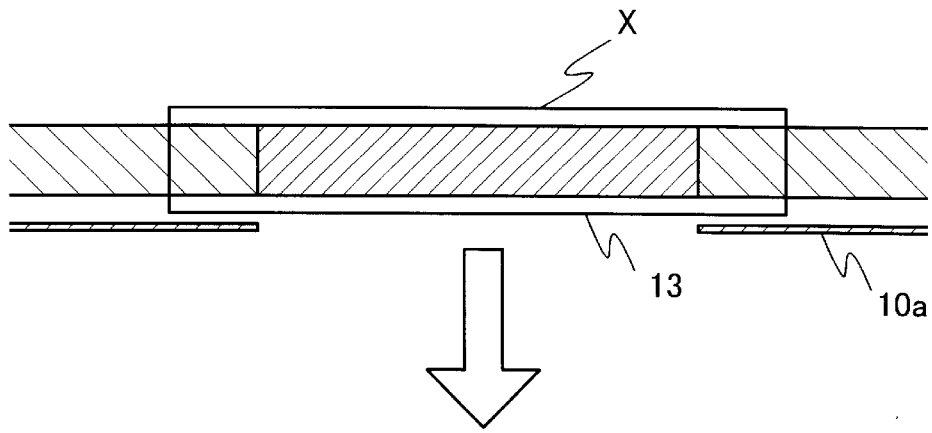
FIG. 22 is a vertical sectional view showing fluorescence emission from a fluorescent glass element in a normal dose reading magazine as illustrated in FIG. 15.
Figure 23:
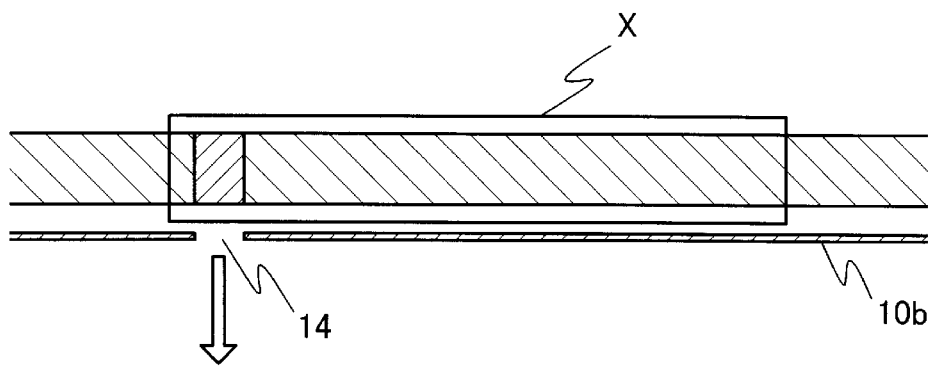
FIG. 23 is a vertical sectional view showing fluorescence emission from a fluorescent glass element in a high dose reading magazine as illustrated in FIG. 14.

At step D808, one of the plurality of fluorescent glass elements accommodated in the magazine is set in the measurement position, and as illustrated by FIG. 18, FIG. 22 and FIG. 23, the fluorescence generated by that fluorescent glass element X is transmitted through the aperture window 13 or aperture hole 14 of the aforementioned magazine, and the fluorescence transmission window 31d of the moving table 31, condensed by the condensing section 55, and detected by the photomultiplier tube 51 (step D809). The detected value is then corrected by the linear correction formula set by the step D803 or step D806 (step D810). The calculated reading result is then displayed by the display section with the units of the reading mode set at step D804 or step D807 (step D811).

It is then judged whether or not the measurement process has been completed for all the fluorescent glass elements accommodated in the magazine (step D812), and if this has not been completed, then the procedure returns to step D808, and the processing in step D809–step D812 is repeated for the next fluorescent glass element. If, on the other hand, the measurement processing has been completed for all fluorescent glass elements accommodated in the magazine, then the dose reading process for that magazine ends.

(C-2-4) Merits

According to the dose reading device of the present embodiment described above, since it is distinguished whether or not the magazine is a normal dose reading magazine 10a or a high dose reading magazine 10b, mode switching can be implemented automatically in order to perform calibration of the detection sensitivity or correction using a linear correction formula, and the like, and hence manual setting tasks are omitted and accurate exposure doses can be calculated, while preventing reading errors due to incorrect settings.

(C-3) Other Embodiments

The present invention is not limited to the embodiment described above, and may be modified appropriately in terms of the size, shape, number, material and type of the respective members, and the like. For example, the magazine may also be designed freely with regard to the structure thereof and the number of fluorescent glass elements accommodated therein, provided that it is capable of accommodating a plurality of fluorescent glass elements, in such a manner that ultraviolet irradiation and fluorescence detection can be performed while the fluorescent glass elements are accommodated therein.

Moreover, it is also possible to distinguish between the normal dose reading magazine and the high dose reading magazine by providing respective structural differences therein other than the apertures described above, or differences for the purpose of identification. Furthermore, the types of magazine are not limited to the two types of magazine described above, and three or more types of magazine may be used. In addition, the material of the magazine should desirably have low or nil fluorescence generation characteristics.

Figure 24:
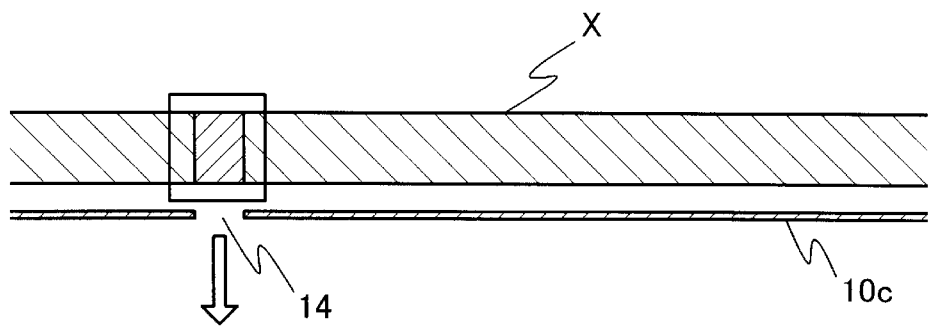
FIG. 24 is a vertical section view showing a fluorescent glass element, being a further embodiment of the present invention.

Moreover, the shape and size of the fluorescent glass elements used may be designed freely. For example, when performing high dose reading, only the end portion thereof on the side of incidence of the ultraviolet laser beam is used, and hence even smaller fluorescent glass elements X can be measured, as illustrated in FIG. 24. Furthermore, the fluorescence reading device to which the present invention is applied is not limited to the examples described in the foregoing embodiments, provided that it allows irradiation of ultraviolet light in order to excite the fluorescent glasses, and detection of the amount of fluorescence.

[D. Dose Reading Device]

The characteristic features of the present invention relate to an optical system for fluorescence reading which is capable of obtaining high detection sensitivity by condensing the very weak light from a small-sized fluorescent glass element used in a dose reading device as described in [A. Dose reading device] above.

(D-1) Composition

Figure 25:
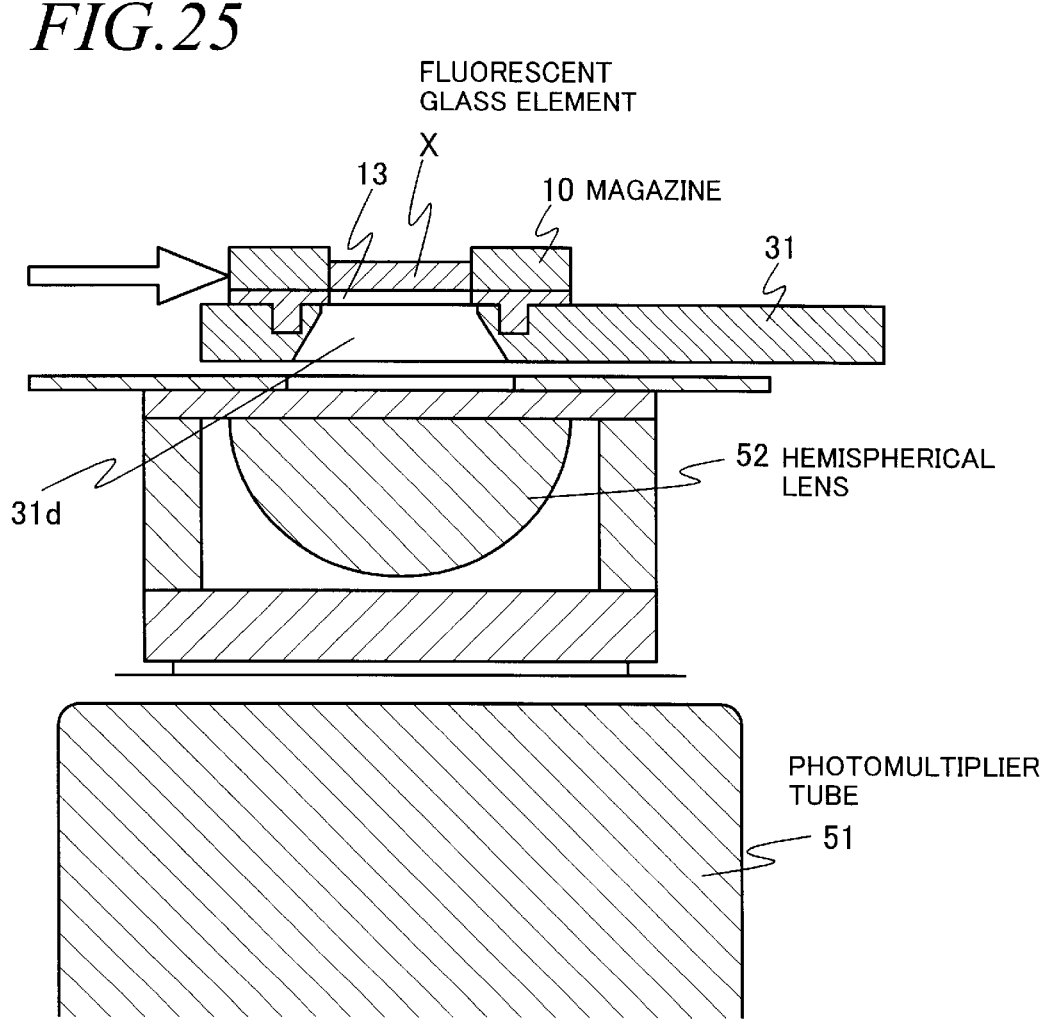
FIG. 25 is a vertical sectional view showing the periphery of a fluorescence detecting section of a dose reading device relating to the present invention.

As shown in FIG. 25, a hemispherical lens 52 forming condensing means is provided between a fluorescent glass element X to be measured and the photomultiplier tube 51 forming a fluorescence detecting element. This photomultiplier tube 51 converts the fluorescence from the fluorescent glass element X to an electrical signal for detection, and the hemispherical lens 52 condenses the fluorescence from the fluorescent glass element X and inputs it to the photomultiplier tube 51.

Figure 26:
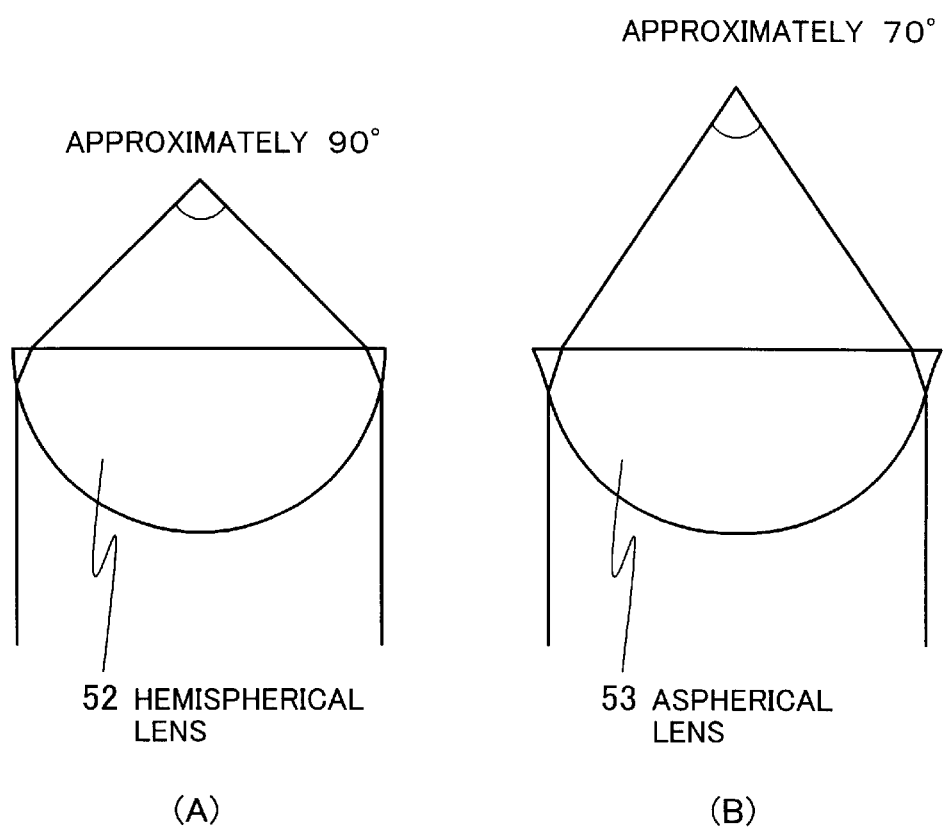
FIG. 26 is a principle diagram showing the difference between the condensable angle (numerical aperture) of a hemispherical lens and an aspherical lens.
Figure 27:
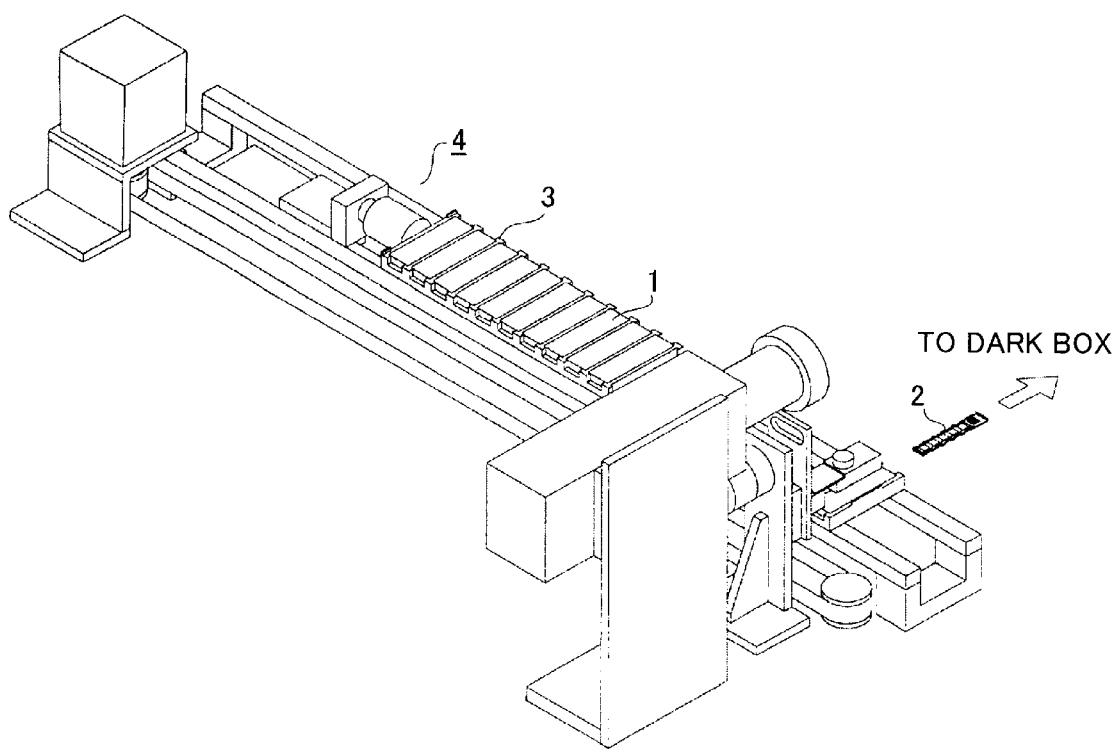
FIG. 27 is a perspective view showing one example of a magazine conveying device in a conventional dose reading device.
Figure 28:
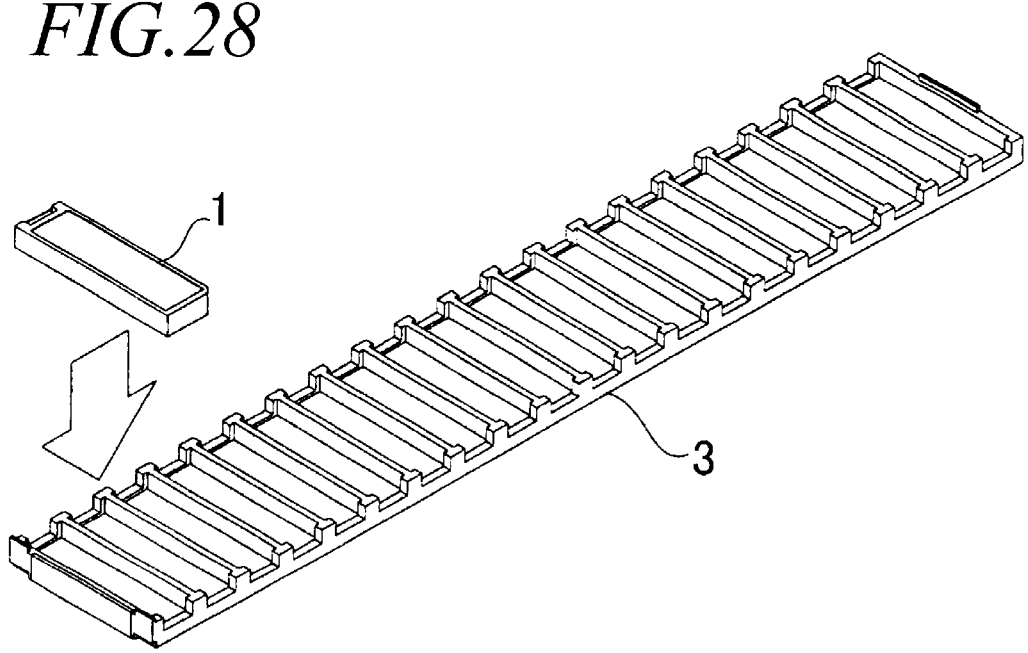
FIG. 28 is a perspective view showing one example of a magazine in a conventional dose reading device.
Figure 29:
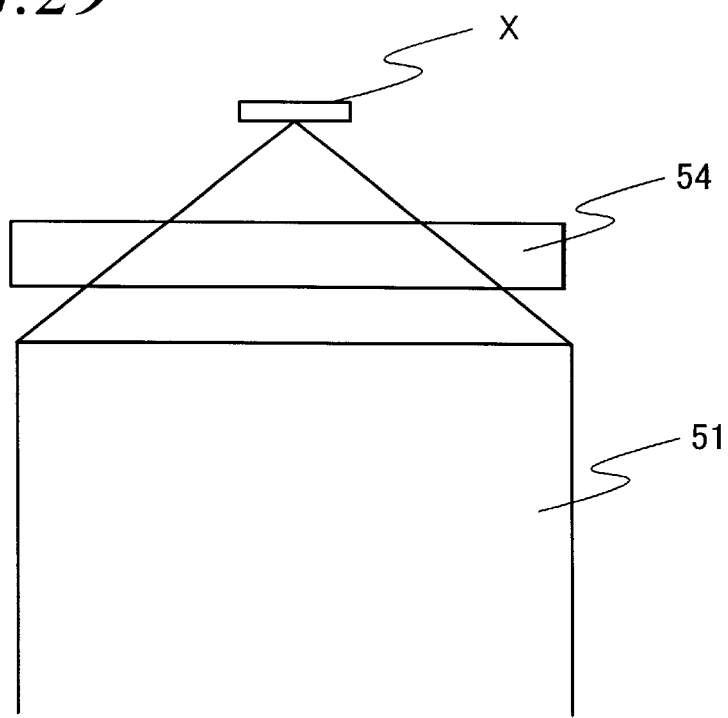
FIG. 29 is a diagram showing the fluorescence incident at the photomultiplier tube in a case where an interference filter is inserted between the fluorescent glass element and the photomultiplier tube.

Besides a hemispherical lens 52, it is also possible to use an aspherical lens or a full spherical lens, in place of the hemispherical lens 52, but for the following reasons, a hemispherical lens 52 is most suitable. Namely, if the lens is an aspherical lens 53, as shown in FIG. 26(B), then the condensable angle is approximately 70° (numerical aperture: approximately 0.57), whereas, as illustrated in FIG. 26(A), if the lens is a hemispherical lens 52, then the condensable angle is approximately 90° (numerical aperture: approximately 0.71), and therefore a greater amount of fluorescence can be condensed.

Furthermore, if a full spherical lens is used, then although the numerical aperture can be increased further than a hemispherical lens, the focal distance is also reduced, and hence the distance from the surface of the full spherical lens to the focal point is reduced excessively, and it becomes difficult to place other members (for example, an ultraviolet excluding filter, magazine, moving table, etc.) between the fluorescent glass element X and the full spherical lens.

In FIG. 25, a composition is adopted wherein the fluorescent glass elements X are accommodated in a magazine 10, which is placed on a moving table 31 provided in the fluorescence reading device, in such a manner that it is set in a fluorescence reading position.

(D-2) Action

In the dose reading device according to the present embodiment having the foregoing composition, a fluorescent glass element X accommodated in the magazine 10 and disposed in the measurement position is excited by an incident ultraviolet laser beam (indicated by the arrow in the diagram), and it generated fluorescence in direct proportion to the exposure dose thereof. As shown in FIG. 25, this fluorescence passes through the aperture window 13 of the magazine 10 and the fluorescence transmission window 31d of the moving table 31, is condensed by the hemispherical lens 52, and is detected by the photomultiplier tube 51.

(D-3) Merits

According to the dose reading device of the present embodiment, since the fluorescence generated by a small-sized fluorescent glass element is condensed by the hemispherical lens 52 and input to an photomultiplier tube 51 forming a detector, the amount of light input to the photomultiplier tube 51 is increased by up to two times compared to cases where a conventional dose reading device is used. Consequently, it is possible to increase detection sensitivity markedly. In particular, by using a hemispherical lens 52, it is possible to concentrate a larger amount of light than in cases where an aspherical lens 53 is used.

Moreover, even if an interference filter is inserted between the fluorescent glass element X and the photomultiplier tube 51, since the fluorescence generated by the fluorescent glass element X is condensed by the hemispherical lens 52, the fluorescence will be virtually parallel after passing through the lens, and hence the transmission wavelength of the interference filter will not be shifted to a shorter wavelength as in the prior art, and the original transmission wavelength characteristics can be obtained.

(D-4) Other Embodiments

The present invention is not limited to the embodiment described above, and may be modified appropriately in terms of the size, shape, number, material and type of the respective members, and the like. For example, if a spherical lens is used instead of a hemispherical lens as the condensing means, then although the amount of light condensed will be reduced, it is still possible to ensure the parallelism of the fluorescence incident on the detecting means. Moreover, the detecting means is not limited to that described in the foregoing embodiment, provided that it is capable of detecting the amount of fluorescence.

Industrial Applicability

As described above, according to the present invention, it is possible to provide a dose reading device capable of performing accurate dose reading, while fluorescent glass elements are in an accommodated state in a magazine.

Furthermore, according to the present invention, it is possible to provide a dose reading magazine and a method of manufacturing same, whereby dose reading is possible while the fluorescent glass elements are in an accommodated state.

Moreover, according to the present invention, it is possible to provide a dose reading magazine, dose reading method and dose reading device, whereby, even in the case of high exposure doses, linear correction can be performed and the radiation exposure dose can be read accurately.

Furthermore, according to the present invention, it is possible to provide a dose reading device, which is capable of obtaining high detection sensitivity, by condensing very weak light from small-sized fluorescent glass elements.

What is claimed is:

1. A dose reading device having an irradiating means for irradiating ultraviolet light forming an excitation light source for a fluorescent glass element, and a detecting means for detecting a radiation exposure dose from the intensity of fluorescence generated by said fluorescent glass element, comprising:

a magazine conveying section for conveying a magazine capable of accommodating a plurality of fluorescent glass elements to the position of a fluorescence detecting part for fluorescence detection by said detecting means; and a dark box section for accommodating said magazine conveying section and said fluorescence detecting part.

2. The dose reading device according to claim 1, further comprising a first shielding plate, which is provided in a position where the ultraviolet light from said irradiating means passes through said fluorescent glass element, being set at a non-perpendicular angle with respect to the light axis of the ultraviolet light.

3. The dose reading device according to claim 1, further comprising a second shielding plate, which is provided between the fluorescent glass element under measurement being positioned at said fluorescence detection part, and said detecting means, for shielding fluorescence from glass elements other than the fluorescent glass element under measurement.

4. The dose reading device according to claim 1, further comprising a first slit plate, which is installed at the ultraviolet light exit position of said irradiating means, for transmitting only ultraviolet light directed at the fluorescent glass element under measurement.

5. The dose reading device according to claim 1, further comprising a second slit plate, which is installed at the ultraviolet light incidence position on the fluorescent glass element under measurement being positioned at said fluorescence detection part, for transmitting only ultraviolet light directed at the fluorescent glass element under measurement.

6. The dose reading device according to claim 2, further comprising a second shielding plate, which is provided between the fluorescent glass element under measurement being positioned at said fluorescence detection part, and said detecting means, for shielding fluorescence from glass elements other than the fluorescent glass element under measurement.

7. The dose reading device according to claim 2, further comprising a first slit plate, which is installed at the ultraviolet light exit position of said irradiating means, for transmitting only ultraviolet light directed at the fluorescent glass element under measurement.

8. The dose reading device according to claim 3, further comprising a first slit plate, which is installed at the ultraviolet light exit position of said irradiating means, for transmitting only ultraviolet light directed at the fluorescent glass element under measurement.

9. The dose reading device according to claim 2, further comprising a second slit plate, which is installed at the ultraviolet light incidence position on the fluorescent glass element under measurement being positioned at said fluorescence detection part, for transmitting only ultraviolet light directed at the fluorescent glass element under measurement.

10. The dose reading device according to claim 3, further comprising a second slit plate, which is installed at the ultraviolet light incidence position on the fluorescent glass element under measurement being positioned at said fluorescence detection part, for transmitting only ultraviolet light directed at the fluorescent glass element under measurement.

11. The dose reading device according to claim 4, further comprising a second slit plate, which is installed at the ultraviolet light incidence position on the fluorescent glass element under measurement being positioned at said fluorescence detection part, for transmitting only ultraviolet light directed at the fluorescent glass element under measurement.

12. A dose reading magazine having loading sections capable of loading a plurality of fluorescent glass elements for reading a radiation exposure dose from the intensity of fluorescence generated upon irradiation of ultraviolet light, comprising:
   an aperture window, which is provided in a prescribed position of said magazine, for allowing the fluorescence generated by said fluorescent glass elements to exit therethrough.

13. The dose reading magazine according to claim 12, wherein a warp having occurred after molding of said dose reading magazine has been corrected by heat treatment in a state where a load is applied in the inverse direction of the warp.

14. The dose reading magazine according to claim 12, being made from a material which generates little fluorescence upon irradiation of ultraviolet light.

15. The dose reading magazine according to claim 13, being made from a material which generates little fluorescence upon irradiation of ultraviolet light.

16. A method of manufacturing a dose reading magazine having loading sections capable of loading a plurality of fluorescent glass elements for reading a radiation exposure dose from the intensity of fluorescence generated upon irradiation of ultraviolet light, comprising:
   correcting a warp having occurred after molding of said dose reading magazine by heat treatment in a state where a load is applied in the inverse direction of the warp.

17. A dose reading magazine capable of loading a fluorescent glass element which generates fluorescence corresponding to the radiation exposure dose thereof, upon irradiation of ultraviolet light, comprising:
   an aperture for allowing only fluorescence from an end portion of said fluorescent glass element on the side of incidence of the ultraviolet light to exit therethrough.

18. A dose reading method for irradiating ultraviolet light forming an excitation light source onto a fluorescent glass element loaded in a dose reading magazine having an aperture for emitting fluorescence, and reading a radiation exposure dose on the basis of the intensity of the fluorescence emitted by said fluorescent glass element via said aperture, comprising:
   judging the type of said dose reading magazine on the basis of the size of the aperture provided in the magazine; and
   calibrating the fluorescence detection sensitivity and correcting the reading values, on the basis of the judgment result.

19. A dose reading device having an irradiating means for irradiating ultraviolet light forming an excitation light source onto a fluorescent glass element loaded in a dose reading magazine having an aperture for emitting fluorescence, and a fluorescence detecting means for reading a radiation exposure dose on the basis of the intensity of the fluorescence emitted from said fluorescent glass element via said aperture, comprising:
   a judging means for judging the type of said dose reading magazine on the basis of the size of the aperture provided in the magazine; and
   a dose reading processing means for calibrating the sensitivity of said fluorescence detecting means and correcting the reading values, on the basis of the judgment results from said judging means.

20. A dose reading device having a detecting means for detecting the radiation exposure dose of a fluorescent glass element on the basis of the intensity of the fluorescence generated by the fluorescent glass element when irradiated with ultraviolet light, comprising:
   a condensing means, which is provided between the fluorescent glass element under detection and said detecting means, for condensing the fluorescence generated by said fluorescent glass element.

21. The dose reading device according to claim 20, wherein said condensing means is a hemispherical lens.

* * * * *